US011017014B2

(12) United States Patent
Ebberson et al.

(10) Patent No.: US 11,017,014 B2
(45) Date of Patent: May 25, 2021

(54) USING SHARED METADATA TO PRESERVE LOGICAL ASSOCIATIONS BETWEEN FILES WHEN THE FILES ARE PHYSICALLY STORED IN DYNAMICALLY-DETERMINED CLOUD-BASED STORAGE STRUCTURES

(71) Applicant: Box, Inc., Redwood City, CA (US)

(72) Inventors: Cody D. Ebberson, San Francisco, CA (US); Reshma K. Ebberson, San Francisco, CA (US)

(73) Assignee: Box, Inc., Redwood City, CA (US)

( * ) Notice: Subject to any disclaimer, the term of this patent is extended or adjusted under 35 U.S.C. 154(b) by 1160 days.

(21) Appl. No.: 15/161,227

(22) Filed: May 21, 2016

(65) Prior Publication Data

US 2017/0024515 A1 Jan. 26, 2017

Related U.S. Application Data

(60) Provisional application No. 62/165,417, filed on May 22, 2015.

(51) Int. Cl.
*G06F 16/51* (2019.01)
*G06F 16/48* (2019.01)
(Continued)

(52) U.S. Cl.
CPC ........ *G06F 16/51* (2019.01); *G06F 16/24573* (2019.01); *G06F 16/27* (2019.01);
(Continued)

(58) Field of Classification Search
CPC ........ G06F 19/321; G06F 16/51; G06F 16/00; G06F 16/27; G06F 16/48; G06F 16/24573; G16H 30/20; G16H 10/60
See application file for complete search history.

(56) References Cited

U.S. PATENT DOCUMENTS

2004/0193621 A1* 9/2004 Moore ................ G06F 16/248
2009/0138789 A1* 5/2009 Tangen ............... G06F 16/258
715/213
(Continued)

OTHER PUBLICATIONS

Mano Marks, "Google Developers: Creating super-overlays with gdal2tiles", (Sep. 2009), URL: https://developers.google.com/kml/articles/raster, (Document indicates that capture date of submitted copy by Archive.org is May 11, 2015).
(Continued)

*Primary Examiner* — Jonathan Durant
(74) *Attorney, Agent, or Firm* — Vista IP Law Group, LLP

(57) ABSTRACT

Systems for accessing medical imagery from a cloud-based facility using a browser-like application. A first user (e.g., a physician) identifies a first plurality of medical digital information files that are organized in a first storage structure. The first user's requests a set of first digital information views of the identified medical digital information of the first storage structure wherein the plurality of first digital information views are described by a respective first set of logical view attributes that are associated with the files organized in the first storage structure. A second user (e.g., a second physician) requests a second plurality of digital information views of the first storage structure wherein the second plurality of digital information. The system sends the first digital information views to the first user, and sends the second digital information views to the second user.

21 Claims, 13 Drawing Sheets

(51) Int. Cl.
*G06F 16/2457* (2019.01)
*G16H 40/67* (2018.01)
*G16H 30/20* (2018.01)
*G06F 16/27* (2019.01)

(52) U.S. Cl.
CPC ............ *G06F 16/48* (2019.01); *G16H 30/20* (2018.01); *G16H 40/67* (2018.01)

(56) References Cited

U.S. PATENT DOCUMENTS

| | | | | |
|---|---|---|---|---|
| 2010/0080427 | A1* | 4/2010 | Yeluri | G06F 19/321 382/128 |
| 2010/0138446 | A1* | 6/2010 | Canessa | G06F 15/16 707/770 |
| 2012/0070045 | A1* | 3/2012 | Vesper | G06Q 50/22 382/128 |
| 2012/0099769 | A1* | 4/2012 | Eichhorn | G06F 19/321 382/128 |
| 2013/0129165 | A1* | 5/2013 | Dekel | G06F 19/321 382/128 |
| 2014/0114672 | A1* | 4/2014 | Wright | G06Q 50/24 705/2 |
| 2014/0126841 | A1* | 5/2014 | Wang | G06F 19/321 382/305 |
| 2014/0279893 | A1* | 9/2014 | Branton | G06F 16/904 707/634 |

OTHER PUBLICATIONS

"Google Developers: Tile Layers", (Apr. 25, 2015), (Mar. 19, 2015), URL: https://developers.google.com/maps/documentation/ios/tiles, (Document indicates that capture date of submitted copy by Archive.org is Apr. 25, 2015).

* cited by examiner

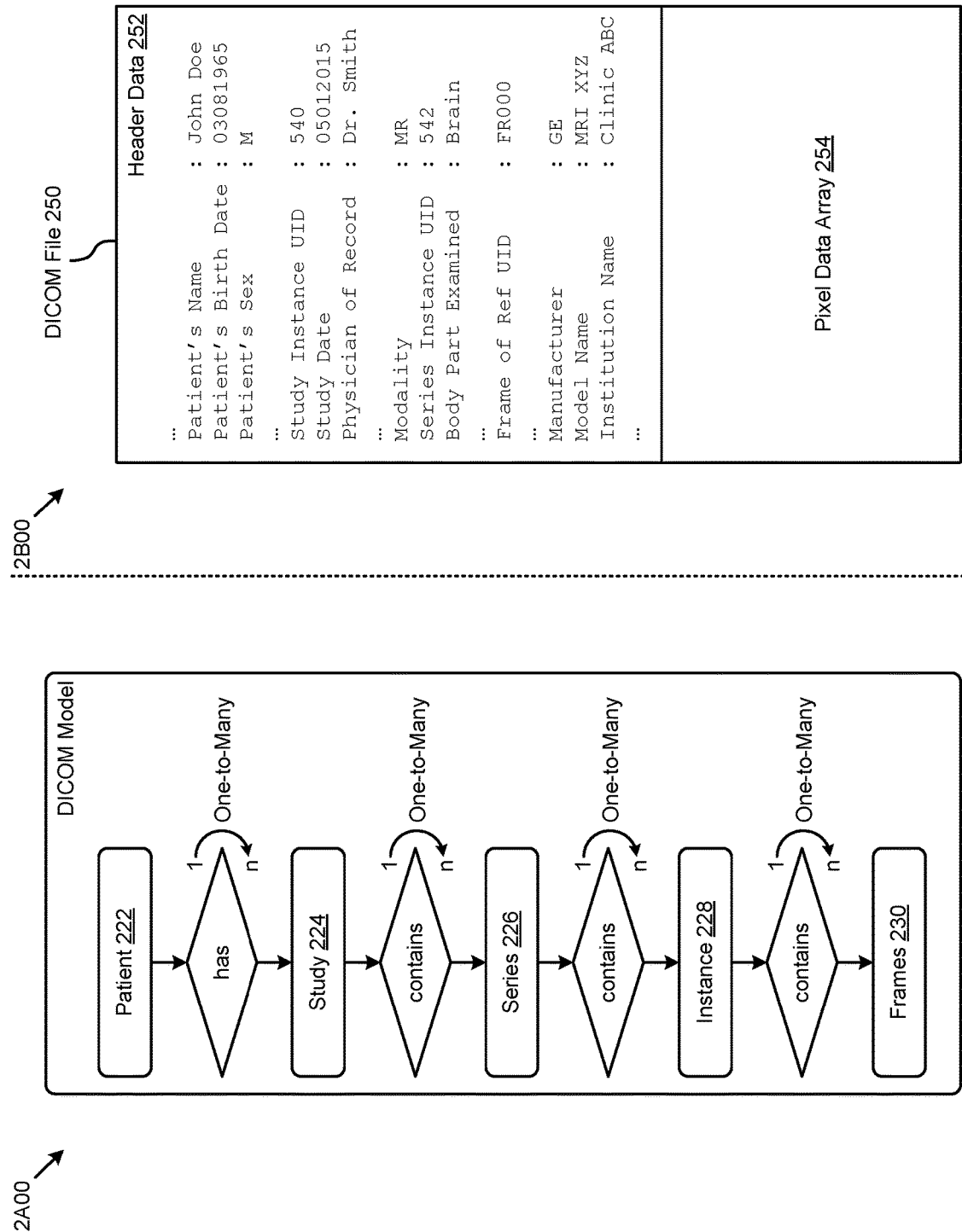

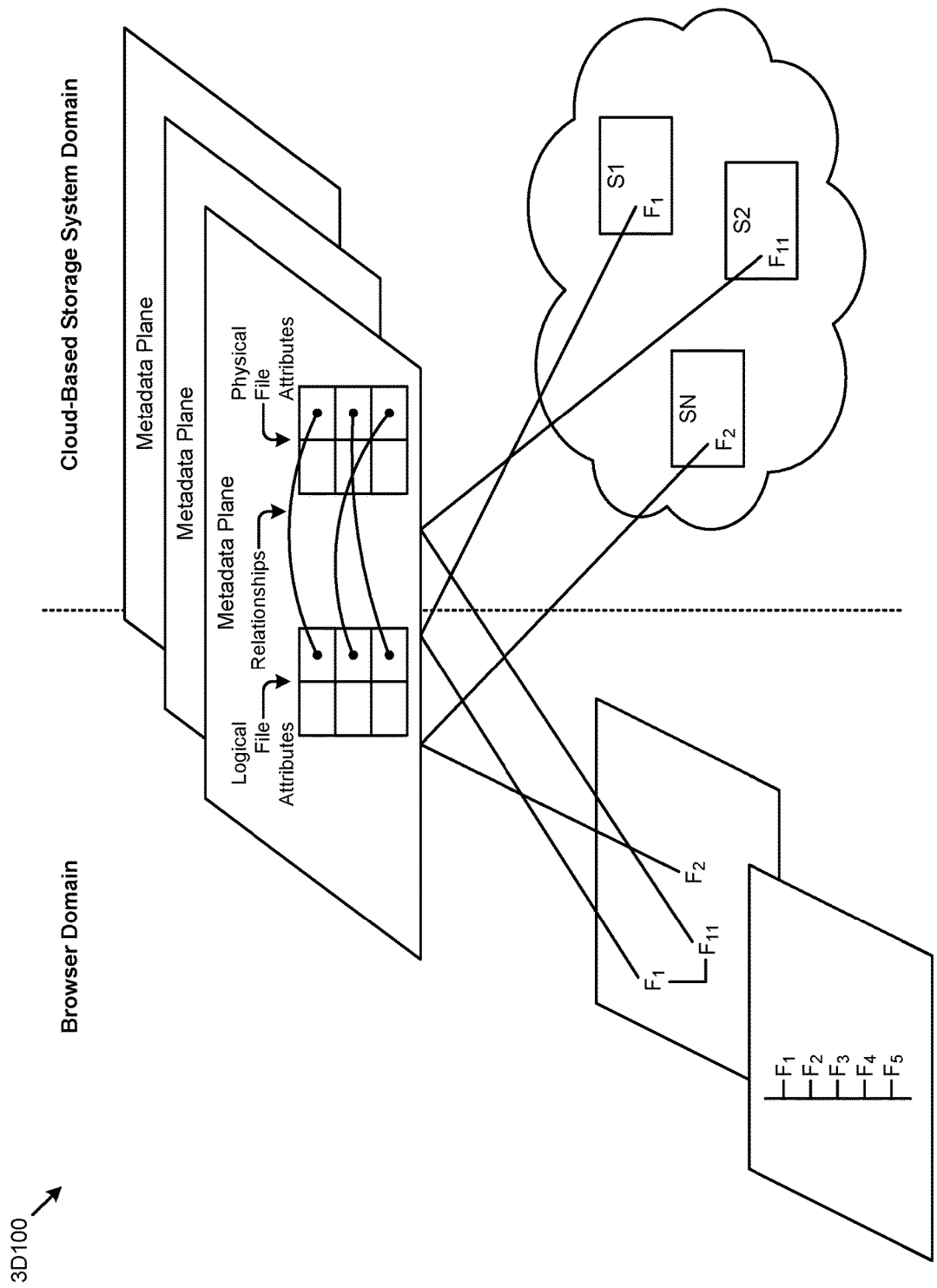
FIG. 3D1

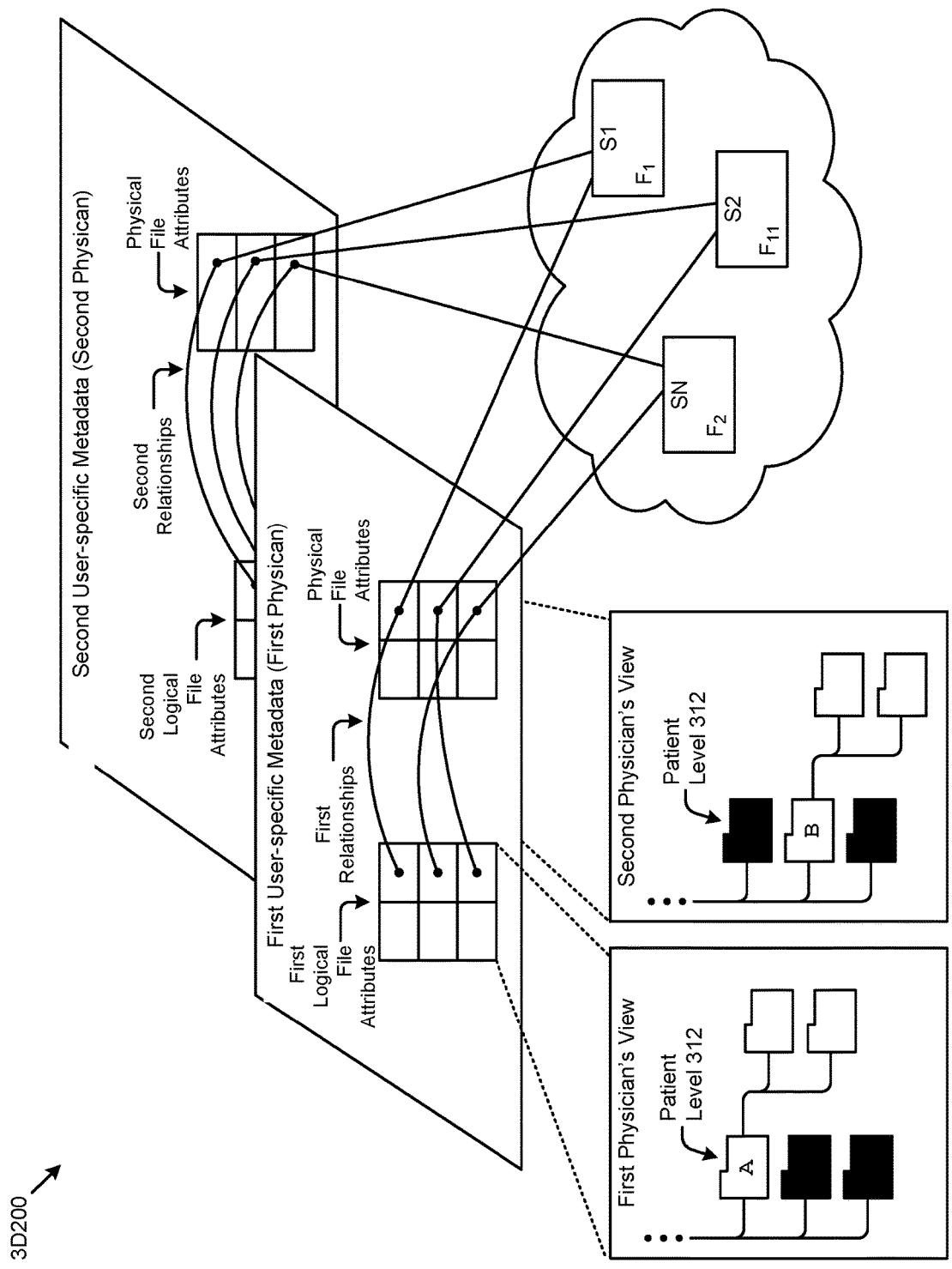
FIG. 3D2

| FileID | PatientName | StudyID | SeriesID | ... |
|---|---|---|---|---|
| ... | | | | |
| 1ae2gh2390 | Doe, John | A | 542 | |
| ... | | | | |
| ewkj4lqt44 | Doe, John | B | 554 | |
| 438dis9wk4 | Doe, John | A | 542 | |
| ... | | | | |
| 9djsd89si4 | Doe, John | B | 556 | |
| kd93kd96js | Last, First | XXXX | YYYY | |
| ... | | | | |

Image File Metadata 194

Associated Files 402

USING SHARED METADATA TO PRESERVE LOGICAL ASSOCIATIONS BETWEEN FILES WHEN THE FILES ARE PHYSICALLY STORED IN DYNAMICALLY-DETERMINED CLOUD-BASED STORAGE STRUCTURES

The present application claims the benefit of priority to U.S. Provisional Patent Application Ser. No. 62/165,417 titled, "USING SHARED METADATA TO PRESERVE LOGICAL ASSOCIATIONS BETWEEN FILES WHEN THE FILES ARE PHYSICALLY STORED IN DYNAMICALLY-DETERMINED CLOUD-BASED STORAGE STRUCTURES", filed on May 22, 2015, and is also cross related to U.S. Patent Application Ser. No. 14/719,758 titled, "RENDERING HIGH RESOLUTION IMAGES USING IMAGE TILING AND HIERARCHICAL IMAGE TILE STORAGE STRUCTURES", filed on May 22, 2015, which are hereby incorporated by reference in their entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD

This disclosure relates to the field of accessing cloud-based data using a browser-like application, and more particularly to techniques for using shared metadata to preserve logical associations between files when the files are physically stored in dynamically-determined cloud-based storage structures.

BACKGROUND

The proliferation of cloud-based storage systems and platforms continues to increase. Specifically, cloud-based content management services and platforms have impacted the manners in which personal and corporate information is stored, and has also impacted the way personal and corporate information are shared and managed. One benefit of using a cloud-based storage system is efficient use of electronic storage facilities and computing resources for storing and sharing digital information files (e.g., "files"). Another benefit of the cloud-based storage system is access to content from anywhere and from any device through a web browser. For example, a cloud-based storage system can store several files owned by a certain user in multiple physical locations (e.g., multiple servers, multiple geographic locations, etc.) to balance and optimize resource usage, yet cloud-based storage systems can present a user defined view of the files (e.g., a directory called "My Files") in a web browser on various user devices that gives the appearance that the files coexist in a single directory on a single storage device.

In some environments, certain files, in particular shared files, can have associations that extend beyond file ownership. For example, medical imaging studies can comprise thousands of image files that are interrelated by certain attributes such as patient name, study identifier, body part, frame of reference, and other attributes. In such cases, file users (e.g., radiologists, etc.) might want to invoke various sequences or images or specific views of images that comprise a certain stack or portions of the image files (e.g., a set of one or more digital information views). For example, the radiologist might want to see the front view of a patient's magnetic resonance imaging (MRI) scan brain study, requiring that the stack of image files associated with the front view be determined, selected, and presented for viewing. Some legacy approaches for finding and displaying associated files implement a specific local directory (e.g., folder) storage architecture (e.g., structure) determined in part by the various types of associations, and relied upon as a file lookup mechanism by an on-premises image file viewer application. In such approaches, however, the specific file/folder organization can vary from application to application, such that a first application may not operate predictably on the file/folder organization of a second application. Further, when sharing such associated files (e.g., for doctors to collaborate on MRI scan brain studies), the physical storage structure might be dynamically determined or changed in a manner that is agnostic to the application-specific directory structures and/or agnostic to the manner by which each individual doctor may want to view the files. This sets up the situation where the cloud-based storage system observes one particular physical storage layout for the files (e.g., for performance or efficiency), yet the logical relationships between associated files might be specific to each individual physician or user. Improved techniques, in particular improved application of technology, are needed to address the problem of quickly finding and rendering a large number of associated image files that are logically interrelated, even though the large number of associated image files are stored in various physical locations and directory structures. What is needed is a technique or techniques to improve the application and efficacy of various technologies as compared with the application and efficacy of legacy approaches.

SUMMARY

The present disclosure provides systems, methods, and computer program products suited to address the aforementioned issues with legacy approaches. More specifically, the present disclosure provides a detailed description of techniques used in systems, methods, and in computer program products for using shared metadata to preserve logical associations between files when the files are physically stored in dynamically-determined, cloud-based storage structures. Certain embodiments are directed to technological solutions for overlaying an access model on top of a plurality of storage models using shared metadata, which embodiments advance the relevant technical fields, as well as advancing peripheral technical fields. The disclosed embodiments modify and improve over legacy approaches. In particular, practice of the disclosed techniques reduces use of computer memory, reduces demand for computer processing power, and reduces communication overhead needed for quickly finding and selecting associated files stored in various cloud-based storage structures. Some embodiments disclosed herein use techniques to improve the functioning of multiple systems within the disclosed environments, and some embodiments advance peripheral technical fields as well. As one specific example, use of the disclosed techniques and devices within the shown environments as depicted in the figures provide advances in the technical field of high-performance computing as well as advances in the technical fields of distributed storage.

Further details of aspects, objectives, and advantages of the disclosure are described below and in the detailed description, drawings, and claims. Both the foregoing general description of the background and the following detailed description are exemplary and explanatory, and are not intended to be limiting as to the scope of the claims.

BRIEF DESCRIPTION OF THE DRAWINGS

The drawings described below are for illustration purposes only. The drawings are not intended to limit the scope of the present disclosure.

FIG. 2A is a diagram of a digital medical information model.

FIG. 2B depicts information file attributes associated with digital medical information as used in systems for using shared metadata to preserve logical associations between files when the files are physically stored in dynamically-determined cloud-based storage structures, according to some embodiments.

FIG. 3D1 is a schematic of an environment for implementing an access model as used in systems for using shared metadata to preserve logical associations between files when the files are physically stored in dynamically-determined cloud-based storage structures, according to some embodiments.

FIG. 3D2 is a schematic of an environment for implementing an access model using partially-shared metadata and partially user-specific metadata, according to some embodiments.

FIG. 4A presents a metadata syntax used for associating digital medical information files in systems for using shared metadata to preserve logical associations between files when the files are physically stored in dynamically-determined cloud-based storage structures, according to some embodiments.

DETAILED DESCRIPTION

Figure 1A:
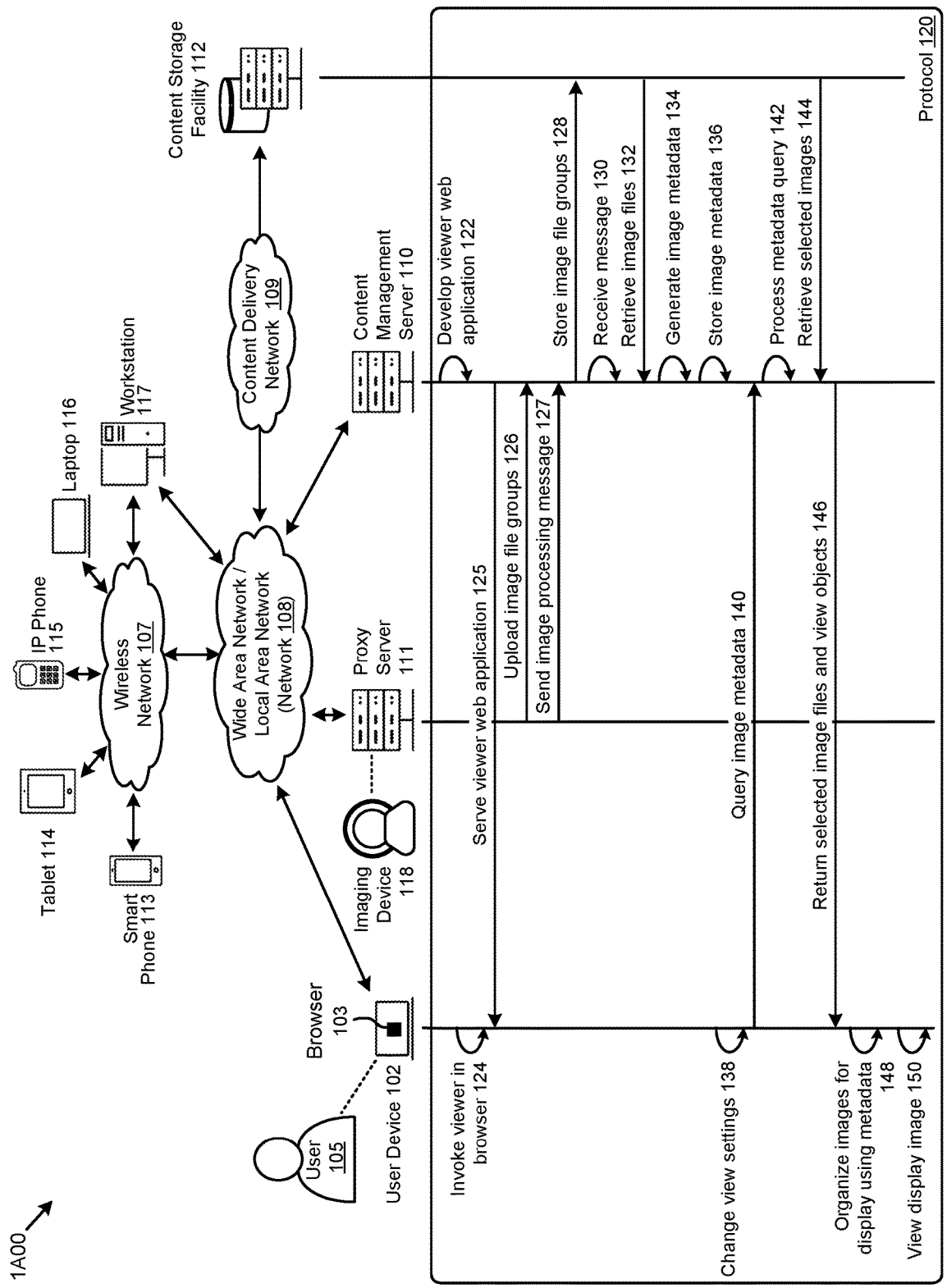
FIG. 1A depicts an environment in which embodiments of the present disclosure can operate.

Some embodiments of the present disclosure address the problem of quickly finding and rendering a large number of associated image files stored in various physical locations and directory structures and some embodiments are directed to approaches for overlaying an access model on top of a plurality of storage models using shared metadata. More particularly, disclosed herein and in the accompanying figures are exemplary environments, systems, methods, and computer program products for using shared metadata to preserve logical associations between files when the files are physically stored in dynamically-determined cloud-based storage structures.

Overview

To address the need for quickly finding and rendering a large number of associated image files stored in various physical locations and directory structures, the techniques described herein discuss (1) identifying digital information files organized in a logical storage organization, (2) identifying associations between the digital information files, (3) storing the digital information files in a physical storage structure, (4) generating metadata describing relationships between the logical storage organization and the physical storage structure, (5) accessing the associated digital information files based on the physical storage structure codified in the metadata, and (6) presenting the digital information files in a browser in accordance with the logical storage organization codified in the metadata.

Various embodiments are described herein with reference to the figures. It should be noted that the figures are not necessarily drawn to scale and that the elements of similar structures or functions are sometimes represented by like reference characters throughout the figures. It should also be noted that the figures are only intended to facilitate the description of the disclosed embodiments—they are not representative of an exhaustive treatment of all possible embodiments, and they are not intended to impute any limitation as to the scope of the claims. In addition, an illustrated embodiment need not portray all aspects or advantages of usage in any particular environment. An aspect or an advantage described in conjunction with a particular embodiment is not necessarily limited to that embodiment and can be practiced in any other embodiments even if not so illustrated. Also, reference throughout this specification to "some embodiments" or "other embodiments" refers to a particular feature, structure, material, or characteristic described in connection with the embodiments as being included in at least one embodiment. Thus, the appearances of the phrase "in some embodiments" or "in other embodiments" in various places throughout this specification are not necessarily referring to the same embodiment or embodiments.

The appended figures discuss aspects in a succession as follows: (1) discussion of an environment in which embodiments of the present disclosure can operate, (2) discussion of a system for using shared metadata to preserve logical associations between files when the files are physically stored in dynamically-determined cloud-based storage structures, (3) presentation of a digital medical information model, and (4) disclosure of information file attributes associated with digital medical information. As one example, the disclosure proposes a patient root hierarchy and an anatomy root hierarchy for storing digital medical information, as well as proposing a metadata syntax for associating digital medical information files. Exemplary systems include implementation of a flow for generating metadata and a process for user image view selections.

Definitions

Some of the terms used in this description are defined below for easy reference. The presented terms and their respective definitions are not rigidly restricted to these definitions—a term may be further defined by the term's use within this disclosure. The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application and the appended claims, the term "or" is intended to mean an inclusive "or" rather than an exclusive "or". That is, unless specified otherwise, or is clear from the context, "X employs A or B" is intended to mean any of the natural inclusive permutations. That is, if X employs A, X employs B, or X employs both A and B, then "X employs A or B" is satisfied under any of the foregoing instances. As used herein, at least one of A or B means at least one of A, or at least one of B, or at least one of both A and B. In other words, this phrase is disjunctive. The articles "a" and "an" as used in this application and the appended claims should generally be construed to mean "one or more" unless specified otherwise or is clear from the context to be directed to a singular form.

Reference is now made in detail to certain embodiments. The disclosed embodiments are not intended to be limiting of the claims.

Descriptions of Exemplary Embodiments

FIG. 1A depicts an environment 1A00 in which embodiments of the present disclosure can operate. As an option, one or more instances of environment 1A00 or any aspect thereof may be implemented in the context of the architecture and functionality of the embodiments described herein. Also, the environment 1A00 or any aspect thereof may be implemented in any desired environment.

As shown in FIG. 1A, environment 1A00 comprises various computing systems (e.g., servers and devices) interconnected by a wireless network 107, a network 108, and a content delivery network 109. The wireless network 107, the network 108, and the content delivery network 109 can comprise any combination of a wide area network (e.g., WAN), local area network (e.g., LAN), cellular network, wireless LAN (e.g., WLAN), or any such means for enabling communication of computing systems. The wireless network 107, the network 108, and the content delivery network 109 can also collectively be referred to as the Internet. The content delivery network 109 can comprise any combination of a public network and a private network. More specifically, environment 1A00 comprises at least one instance of a content management server 110, at least one instance of a proxy server 111, and at least one instance of a content storage facility 112. The servers and storage facilities shown in environment 1A00 can represent any single computing system with dedicated hardware and software, multiple computing systems clustered together (e.g., a server farm), a portion of shared resources on one or more computing systems (e.g., a virtual server), or any combination thereof. For example, the content management server 110 and the content storage facility 112 can comprise a cloud-based content management platform that provides content management and storage services.

Environment 1A00 further comprises an instance of a user device 102 that can represent one of a variety of other computing devices (e.g., a smart phone 113, a tablet 114, an IP phone 115, a laptop 116, a workstation 117, etc.) having software (e.g., a browser 103, an application, etc.) and hardware (e.g., a graphics processing unit, display, monitor, etc.) capable of processing and displaying information (e.g., web page, graphical user interface, etc.) on a display. The user device 102 can further communicate information (e.g., web page request, user activity, electronic files, etc.) over the wireless network 107, the network 108, and the content delivery network 109. As shown, the user device 102 can be operated by an instance of a user 105. Further, an imaging device 118 (e.g., MRI scanner, CT scanner, X-ray scanner, etc.) can be coupled to the proxy server 111, can capture associated images that can be stored in associated medical information files (e.g., medical image files, digital imaging and communications in medicine (DICOM) files), and can send the files to the proxy server 111 for various operations. The medical information files can be hierarchical image tiles as further described in U.S. Patent Application Ser. No. 14/719,758 titled, "RENDERING HIGH RESOLUTION IMAGES USING IMAGE TILING AND HIERARCHICAL IMAGE TILE STORAGE STRUCTURES", filed May 22, 2015.

As shown, the user device 102, the proxy server 111, the content management server 110, and the content storage facility 112 can exhibit a set of high-level interactions (e.g., operations, messages, etc.) in a protocol 120. Specifically, the protocol 120 can represent interactions in systems for using shared metadata to preserve logical associations between files when the files are physically stored in dynamically-determined cloud-based storage structures. As shown, a viewer web application for a browser (e.g., browser 103) can be developed (operation 122) and delivered (e.g., served by a web server) from the content management server 110 to the user device 102 (message 125) in response to the user 105 invoking the viewer in the browser 103 (operation 124). For example, the viewer web application can comprise software instructions (e.g., HTML code, Javascript, PHP code, scripts, etc.) for performing various operations (e.g., image rendering, user event capturing, view querying, network communications, etc.). Certain groups of image files can be captured on the imaging device 118 and securely uploaded by the proxy server 111 to the content management server 110 (message 126). For example, all the files for certain patients and/or certain studies might be uploaded for collaboration purposes. Such files might be associated by certain attributes such as patient name, study identifier, body part, frame of reference, and other attributes. The proxy server 111 can also send image information (e.g., size, filename, etc.) and processing instructions in a message (e.g., HTTP call) to the content management server 110 (message 127). The content management server 110 can store the file groups in the content storage facility 112 (message 128) and poll for any related image processing messages. For example, the file groups can be stored in dynamically-determined cloud-based storage structures that minimize the use of computing and storage resources. When an image processing message is received (operation 130), the content management server 110 can retrieve the stored image files related to the processing message from the content storage facility 112 (message 132) and generate image metadata as specified in the image process message (operation 134). For example, according to the herein disclosed techniques, the image metadata can comprise the aforementioned file associations. The content management server 110 can store the image metadata (message 136), which metadata can be shared in whole or in part with two or more users of the content management server. In some cases portions of metadata are shared, and portions are specific to a particular user.

When a user 105 changes the view settings (e.g., select brain MRI scan front view) from the viewer web application (operation 138), a query of the image metadata can be sent to the content management server 110 (message 140) to determine the associated files required for the new view setting. The view settings (e.g., logical view attributes) can be specific to each individual user. The content management server 110 can process the metadata query (operation 142) and retrieve the selected images from the content storage facility 112 (message 144) to return the selected image files to the user device 102 (message 146). The viewer web application operating on the user device 102 can then organize the selected image files for display (operation 148) for viewing by the user 105 on user device 102 (operation 150).

According to the herein disclosed techniques, by querying the metadata to determine the associated image files corresponding to the new view settings, the associated image files can be quickly and efficiently identified and retrieved for rendering, yet the associated image files can be stored in various physical locations and directory structures as determined by the content management server 110 and/or by the content storage facility 112. One embodiment of a system for implementing the techniques shown in protocol 120 for using shared metadata to preserve logical associations between files when the files are physically stored in dynamically-determined cloud-based storage structures is shown in FIG. 1B.

Figure 1B:
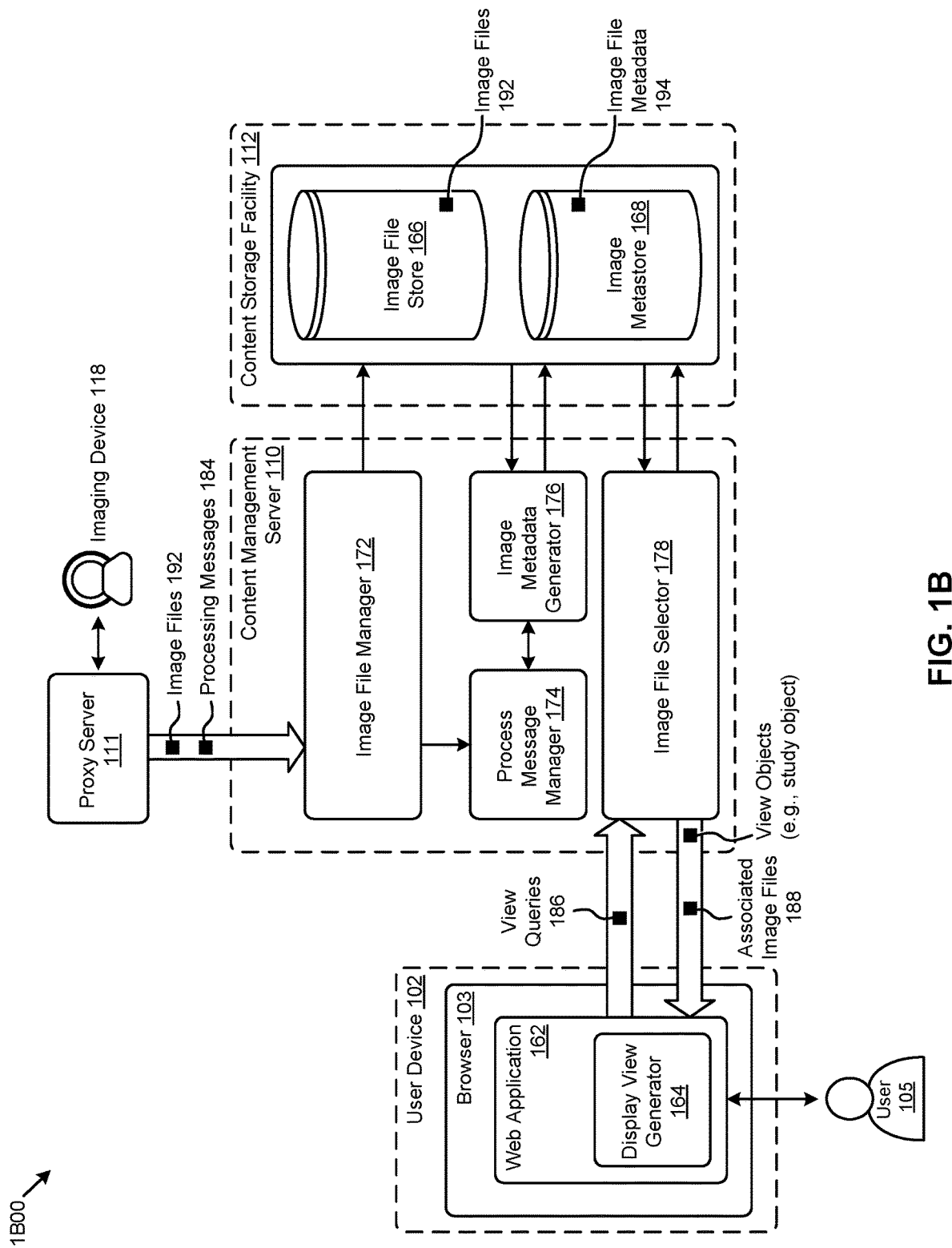
FIG. 1B depicts a system for using shared metadata to preserve logical associations between files when the files are physically stored in dynamically-determined cloud-based storage structures, according to an embodiment.

FIG. 1B depicts a system 1B00 for using shared metadata to preserve logical associations between files when the files are physically stored in dynamically-determined cloud-based storage structures. As an option, one or more instances of system 1B00 or any aspect thereof may be implemented in the context of the architecture and functionality of the embodiments described herein. Also, the system 1B00 or any aspect thereof may be implemented in any desired environment.

The system 1B00 shown in FIG. 1B presents an example embodiment of various modules for implementing the herein disclosed techniques, and operated by the user device 102 and the content management server 110 from environment 1A00. The content storage facility 112, the proxy server 111, and the imaging device 118 from environment 1A00 are also shown for reference. Specifically, the user device 102 can operate a web application 162 comprising a display view generator 164, and the content management server 110 can operate an image file manager 172, a process message manager 174, an image metadata generator 176, and an image file selector 178. As shown, the image file manager 172 can receive image files 192 and processing messages 184 from the proxy server 111 or another computing device. The image file manager 172 can store the received image files 192 in an image file store 166 in the content storage facility 112, and also forward the processing messages 184 to the process message manager 174. In one or more embodiments, the process message manager 174 can continually poll for new messages and take action when a new message is received. For example, a received message may specify that a certain instance or group of instances included in the image files 192 be retrieved for processing by the image metadata generator 176. Specifically, the image metadata generator 176 can process image files to generate a file attribute dataset such as image file metadata 194. Image file metadata serves to codify certain attributes of the files. The image file metadata 194 can be stored for multiple user access (e.g., shared) in an image metadata store 168. In one example case, the image metadata generator 176 can parse the header data of a DICOM image file to extract file attributes and organize (e.g., in a table) the attributes in the image file metadata 194 for various purposes.

Continuing this example, and as shown, when a new view setting specified by the user 105 is received by the web application 162, then view queries 186 comprising view attributes (e.g., patient name, study identifier, frame of reference, etc.) can be sent to the image file selector 178. The image file selector 178 can use the information in the view queries 186 and the image file metadata 194 to determine the associated image files 188 required to render the view desired by the user 105. The display view generator 164 in the web application 162 can then organize (e.g., in a series stack) the associated image files 188 for viewing by the user 105 on user device 102. Further details of a digital medical information model that can be used in system 1B00 and other embodiments is described as pertains to FIG. 2A.

FIG. 2A is a diagram of a digital medical information model 2A00. As an option, one or more instances of digital medical information model 2A00 or any aspect thereof may be implemented in the context of the architecture and functionality of the embodiments described herein. Also, the digital medical information model 2A00 or any aspect thereof may be implemented in any desired environment.

The embodiment shown in FIG. 2A is merely one example of a digital medical information model that describes an association of digital information files (e.g., comprising image data) that can be used with techniques for using shared metadata to preserve logical associations between files when the files are physically stored in dynamically-determined cloud-based storage structures. Specifically, the digital medical information model 2A00 corresponds a certain instance of a DICOM file association structure that shows the "Patient" information entity can be the parent information entity (entity 222) and have a one-to-many (e.g., 1:n) relationship with the "Study" information entity (entity 224). For example, one patient (e.g., John Doe) might have a MRI scan brain study and a CAT scan brain study. Further, a "Study" can have a one-to-many relationship with the "Series" information entity (entity 226), such as for different views in a study, and "Series" can have a one-to-many relationship with the "Instance" information entity (entity 228). Also, as shown, "Instance" can have a one-to-many relationship with the "Frames" information entity (entity 230). In some cases, "Instance" can have a one-to-one relationship (e.g., n=1) with "Frames" (e.g., where an "Instance" comprises one image).

FIG. 2B depicts an example of information file attributes 2B00 associated with digital medical information as used in systems for using shared metadata to preserve logical associations between files when the files are physically stored in dynamically-determined cloud-based storage structures. As an option, one or more instances of the information file attributes 2B00 or any aspect thereof may be implemented in the context of the architecture and functionality of the embodiments described herein. Also, the information file attributes 2B00 or any aspect thereof may be implemented in any desired environment.

FIG. 2B comprises a DICOM file 250 further comprising a portion of header data 252 and a pixel data array 254. Specifically, the header data 252 comprises key-value information (e.g., attributes) pertaining to the DICOM file 250. For example, and as shown, the header data 252 indicates the image file is related to a patient named "John Doe" (e.g., key="Patient's Name" and value="John Doe"), a study instance unique identifier of "540", an examined body part of "Brain", a frame of reference unique identifier "FR000", and other attributes. In legacy approaches for finding and displaying associated files (e.g., all files associated with study "540"), such attributes can be used to determine a specific local directory storage structure for use as a file lookup mechanism by an on-premises image file viewer application. Examples of such approaches are presented in FIG. 3A and FIG. 3B.

Figure 3A:
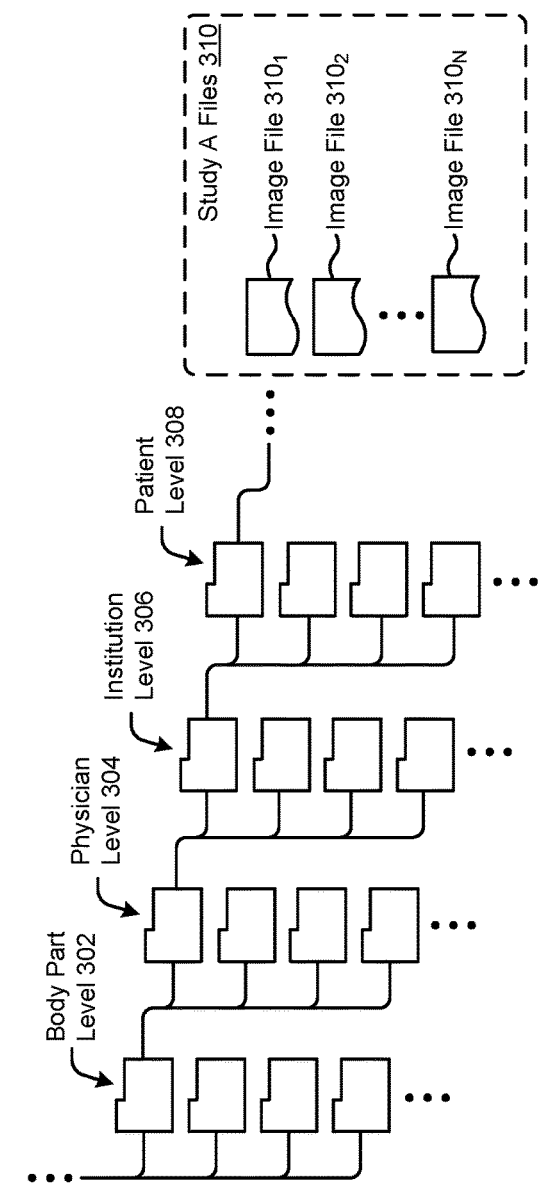
FIG. 3A presents a patient root hierarchy for storing digital medical information in systems for using shared metadata to preserve logical associations between files when the files are physically stored in dynamically-determined cloud-based storage structures, according to some embodiments.

FIG. 3A presents a patient root hierarchy 3A00 for storing digital medical information in systems for using shared metadata to preserve logical associations between files when the files are physically stored in dynamically-determined cloud-based storage structures. As an option, one or more instances of patient root hierarchy 3A00 or any aspect thereof may be implemented in the context of the architecture and functionality of the embodiments described herein. Also, the patient root hierarchy 3A00 or any aspect thereof may be implemented in any desired environment.

As shown, the patient root hierarchy 3A00 is a directory storage architecture that can be used to organize certain associated Study A files 310 (e.g., image file $310_1$, image file $310_2$, . . . , image file $310_N$) to enable a user and/or an on-premises image file viewer application to find and select the files for various operations (e.g., rendering). The associated Study A files 310 shown are an example, and other associated files can also be stored in the patient root hierarchy 3A00. In some cases, the directory levels in the patient root hierarchy 3A00 can correspond to certain attributes (e.g., in the file header data) of the stored files. Specifically, the patient root hierarchy 3A00 has a top parent level that can be a body part level 302 comprising folders corresponding to the body part attribute (e.g., "Brain", "Spine", etc.) of the stored files. The next level in the hierarchy can be a physician level 304, followed by an institution level 306, and a patient level 308. Further child directory levels are possible. As an example, referring to the header data 252 in FIG. 2B, the associated Study A files 310 can correspond to a view (e.g., series, stack of images) for a "Brain" study prescribed by "Dr. Smith" at "Clinic ABC" as pertains to patient "John Doe".

Figure 3B:
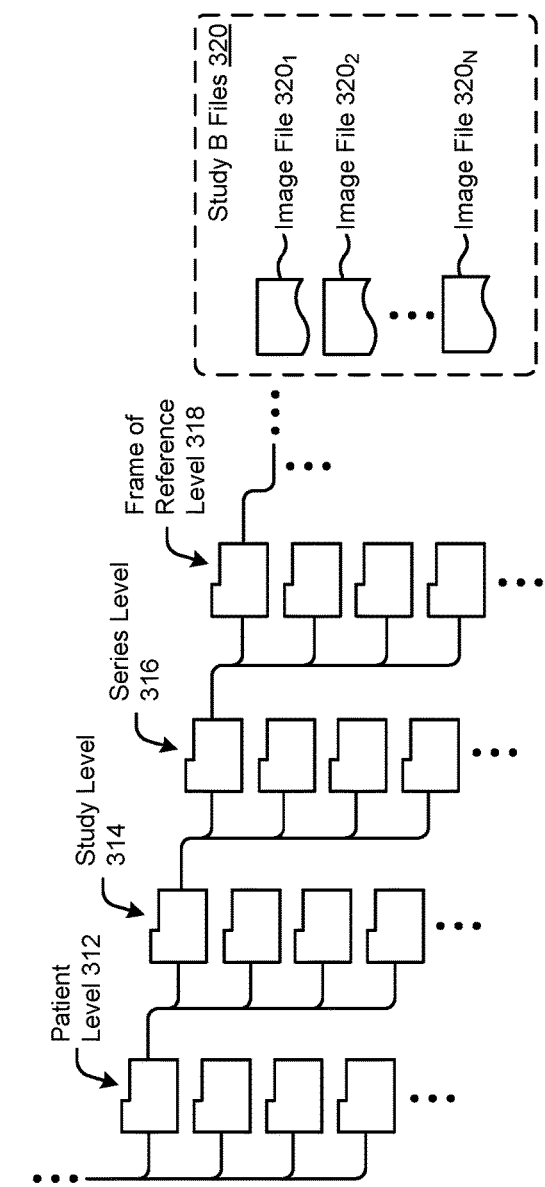
FIG. 3B presents an anatomy root hierarchy for storing digital medical information in systems for using shared metadata to preserve logical associations between files when the files are physically stored in dynamically-determined cloud-based storage structures, according to some embodiments.

FIG. 3B presents an anatomy root hierarchy 3B00 for storing digital medical information in systems for using shared metadata to preserve logical associations between files when the files are physically stored in dynamically-determined cloud-based storage structures. As an option, one or more instances of anatomy root hierarchy 3B00 or any aspect thereof may be implemented in the context of the architecture and functionality of the embodiments described herein. Also, the anatomy root hierarchy 3B00 or any aspect thereof may be implemented in any desired environment.

As shown, the anatomy root hierarchy 3B00 is a directory storage architecture that can be used to organize certain associated Study B files 320 (e.g., image file $320_1$, image file $320_2$, . . . , image file $320_N$) to enable a user and/or an on-premises image file viewer application to find and select the files for various operations (e.g., rendering). The associated Study B files 320 shown are an example, and other associated files can also be stored in the anatomy root hierarchy 3B00. In some cases, the directory levels in the anatomy root hierarchy 3B00 can correspond to certain attributes (e.g., in the file header data) of the stored files. Specifically, the anatomy root hierarchy 3B00 has a top parent level than can be a patient level 312 comprising folders corresponding to the patient attribute (e.g., "P1", "P2", etc.) of the stored files. The next level in the hierarchy can be a study level 314, followed by a series level 316, and a frame of reference level 318. Further child directory levels are possible. As an example, referring to the header data 252 in FIG. 2B, the associated Study B files 320 can correspond to a view (e.g., stack of images) of a patient "John Doe" study "540" that has an image series "542" from a frame of reference "FR000".

The patient root hierarchy 3A00 shown in FIG. 3A and anatomy root hierarchy 3B00 shown in FIG. 3B can be used by on-premises image viewer applications in legacy approaches for finding and viewing (e.g., rendering) associated files (e.g., associated Study A files 310, associated Study B files 320). However, when implementing a cloud-based storage system for such associated files (e.g., for storing and sharing the associated Study A files 310 and the associated Study B files 320), the most efficient storage structure might be dynamically determined, and the application-specific directory structures (e.g., patient root hierarchy 3A00 and anatomy root hierarchy 3B00) may not be retained. One embodiment and example of such a dynamically-determined cloud-based storage structure is described as pertains to FIG. 3C.

Figure 3C:
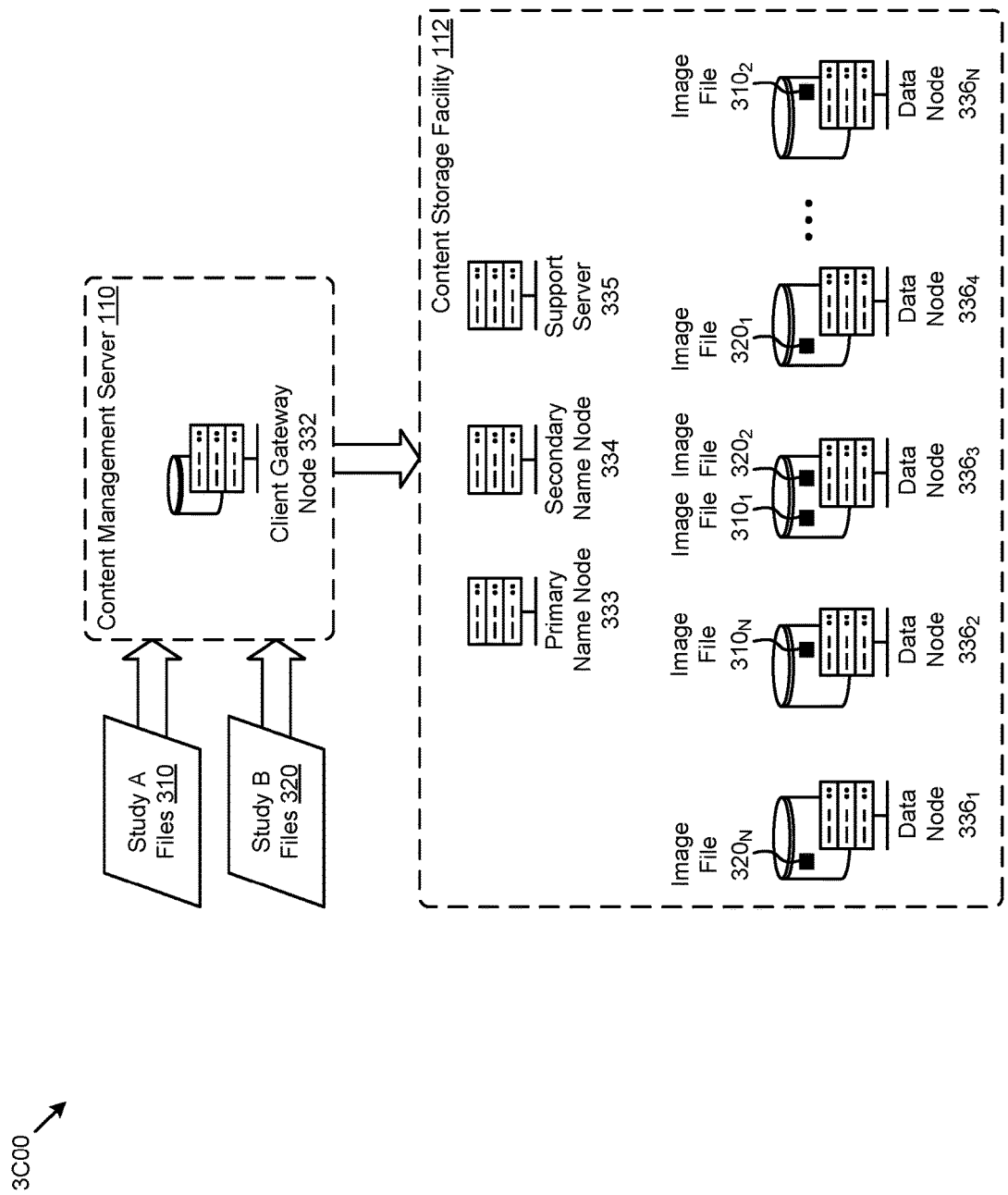
FIG. 3C is a schematic of an environment for implementing a content management storage service as used in systems for using shared metadata to preserve logical associations between files when the files are physically stored in dynamically-determined cloud-based storage structures, according to some embodiments.

FIG. 3C is a schematic 3C00 of an environment for implementing a content management storage service as used in systems for using shared metadata to preserve logical associations between files when the files are physically stored in dynamically-determined cloud-based storage structures. As an option, one or more instances of schematic 3C00 or any aspect thereof may be implemented in the context of the architecture and functionality of the embodiments described herein. Also, the schematic 3C00 or any aspect thereof may be implemented in any desired environment.

As shown, the schematic 3C00 comprises the content management server 110 and the content storage facility 112 from FIG. 1A and FIG. 1B. More specifically, the content management server 110 and the content storage facility 112 can be configurable to store and process large volumes of data and comprise one or more instances of a client gateway node 332, one or more instances of a primary name node 333, one or more instances of a secondary name node 334, one or more instances of a support server 335 (e.g., executing data analysis processes, etc.), and a plurality of data nodes (e.g., data node $336_1$, data node $336_2$, data node $336_3$, data node $336_4$, . . . , and data node $336_N$). Other configurations, partitions, and architectures of the content management server 110 and the content storage facility 112 shown in schematic 3C00 are possible. Further, the content management server 110 and the content storage facility 112 can represent any database management system.

In some embodiments, the content storage facility 112 is configurable to store large files of data across multiple computing devices (e.g., the plurality of data nodes), rather than store all of the files on a single computing device with a large amount of storage capacity. To accommodate such distributed storage, the plurality of data nodes can be configured with one or more rack-mounted servers coupled (e.g., using SATA or SAS interconnects) to multiple hard disk drives for storing the data. In some cases, the physical storage location (e.g., server location) can be dynamically determined based in part on certain parameters such as available storage resources, available computing resources, file size, file format, and other parameters. As an example, when the associated Study A files 310 and the associated Study B files 320 are uploaded to a cloud-based storage system (e.g., the content management server 110 and the content storage facility 112), the files comprising the associated Study A files 310 and the files comprising the associated Study B files 320 can be stored on various data nodes in the content storage facility 112. Specifically, and as shown, the image file $320_N$ can be stored on the data node $336_1$, the image file $310_N$ can be stored on the data node $336_2$, the image file $310_1$ and the image file $320_2$ can be stored on the data node $336_3$, the image file $320_1$ can be stored on the data node $336_4$, and the image file $310_2$ can be stored on the data node $336_N$.

In the environment shown in schematic 3C00, the respective directory storage structures of the Study A files 310 and the Study B files 320 used by on-premises image viewer applications do not need to be captured or retained, yet a cloud-based storage system browser application (e.g., web application 162) must still efficiently render the selected views. The herein disclosed techniques use metadata to preserve logical associations between files even when the files are physically stored in dynamically-determined cloud-based storage structures (e.g., to enable quick discovery and rendering of such files using an access model).

FIG. 3D1 is a schematic of an environment for implementing an access model 3D100 as used in systems for using shared metadata to preserve logical associations between files when the files are physically stored in dynamically-determined cloud-based storage structures, according to some embodiments.

The access model 3D100 relates a set of files (e.g., F1, F2, F3, F4, F5, F11, etc.) that are stored in a particular logical organization to copies or representations of the same files as stored in a particular physical organization. As shown, file F1 and its logical child, file F11 are stored in a first storage location in a browser domain. The access model 3D100 includes any number of metadata planes that in turn can comprise any number of logical file to physical file relationships. Any logical file to physical file relationships (or physical file to logical file relationships) may have associated file attributes, as shown. The aforementioned particular logical organization might be a linear list (e.g., $F_1 \rightarrow F_2 \rightarrow F_3 \rightarrow F_4 \rightarrow F_5$), or might have aspects of a hierarchical logical organization (e.g., $F_{11}$ is a child of $F_1$). The metadata plane can include metadata files that correspond to a particular (e.g., pre-defined) syntax. Any syntax can be used. The syntax supports semantics that include logical file to physical file relationships and/or physical file to logical file relationships, and any file or relationship may have one or more associated attributes. In exemplary embodiments the syntax supports many sets of logical file attributes for any single given set of physical file relationships. Strictly as examples, the file F1 is stored at server S1, the file F11 is stored at server S2, and the file F2 is stored at server SN. The physical partitioning of file storage can span broad geographies, and can include multiple instance copies of the same file at multiple geographic locations. Such partitioning can be captured using an appropriate syntax for metadata. Further, using an appropriate syntax for metadata, different users (e.g., physicians) can choose to view the files differently from another user, even though the physical files are stored in the same location at servers, and even though the files are made accessible for many users. One embodiment and example of such user-specific metadata is described as pertains to FIG. 3D2.

FIG. 3D2 is a schematic 3D200 of an environment for implementing an access model using partially-shared metadata and partially user-specific metadata.

Consider the case where a set of files or objects are shared between a group of physicians. Further consider that not all of the files or objects are shared between every physician (e.g., due to HIPPA rules, etc.). This situation highlights need for implementing an access model (1) using partially-shared metadata, and (2) partially user-specific metadata. As discussed in the foregoing FIG. 3D1, sharing files that are stored in a particular logical organization might be stored in a particular physical organization. However, although the metadata describing the physical storage of the objects may be the same for all users, different physician can see different views, based on metadata.

As shown, a first physician's view includes a view of data pertaining to PatientA (and not other patients). A second physician's view includes a view of data pertaining to PatientB (and not other patients). The relationship between the particular metadata describing the physician's view and the metadata describing the physical storage of the objects can be captured by the relationships between the two types of metadata, as shown. More specifically, the user-specific metadata (e.g., physician-specific) and the partially-shared metadata (e.g., the metadata describing the physical storage of the objects) can be captured by relationships, as shown.

The foregoing is merely an example pertaining to different access models based on dynamically-generated metadata that comprises a portion of partially-shared metadata (e.g., describing physical storage characteristics) and partially user-specific metadata (e.g., per physician). This situation highlights need for implementing an access model by physician's access to a patient or patients, however the same or similar metadata techniques can be applied from implementing an access model by institution, or by study, or by institution to a particular set of studies, or by institution to a particular patient, etc.

One embodiment and example of metadata syntax according to the herein disclosed techniques are described as pertains to FIG. 4A.

FIG. 4A presents a metadata syntax 4A00 used for associating digital medical information files in systems for using shared metadata to preserve logical associations between files when the files are physically stored in dynamically-determined cloud-based storage structures. As an option, one or more instances of metadata syntax 4A00 or any aspect thereof may be implemented in the context of the architecture and functionality of the embodiments described herein. Also, the metadata syntax 4A00 or any aspect thereof may be implemented in any desired environment.

The embodiment shown in FIG. 4A is merely one example of syntax that can be used to organize metadata for describing certain file associations for finding and rendering a large number of associated image files stored in various physical locations and directory structures. The metadata described by the metadata syntax 4A00 provides an access model that can be overlayed on top of a plurality of storage models to enable fast selection and retrieval of certain associated files (e.g., for a given medical view series). Specifically, the metadata syntax 4A00 illustrates an instance of image file metadata 194 having a column and row format comprising various columns corresponding to certain file attributes (e.g., FileID, PatientName, StudyID, SeriesID, etc.). For example, FileID can correspond to a unique identifier assigned to a file at upload that describes the file location in the content storage facility 112. Specifically, the FileID can be used to build a URL for file retrieval (e.g., www.datanode3364.com/getfile?fileid=1ae2gh2390). Other columns in metadata syntax 4A00 can describe file attributes that can be extracted from certain file header data (e.g., header data 252). For example, the PatientName column can correspond to the header data key "Patient's Name", the StudyID column can correspond to the header data key "Study Instance ID", and so on.

Figure 4B:
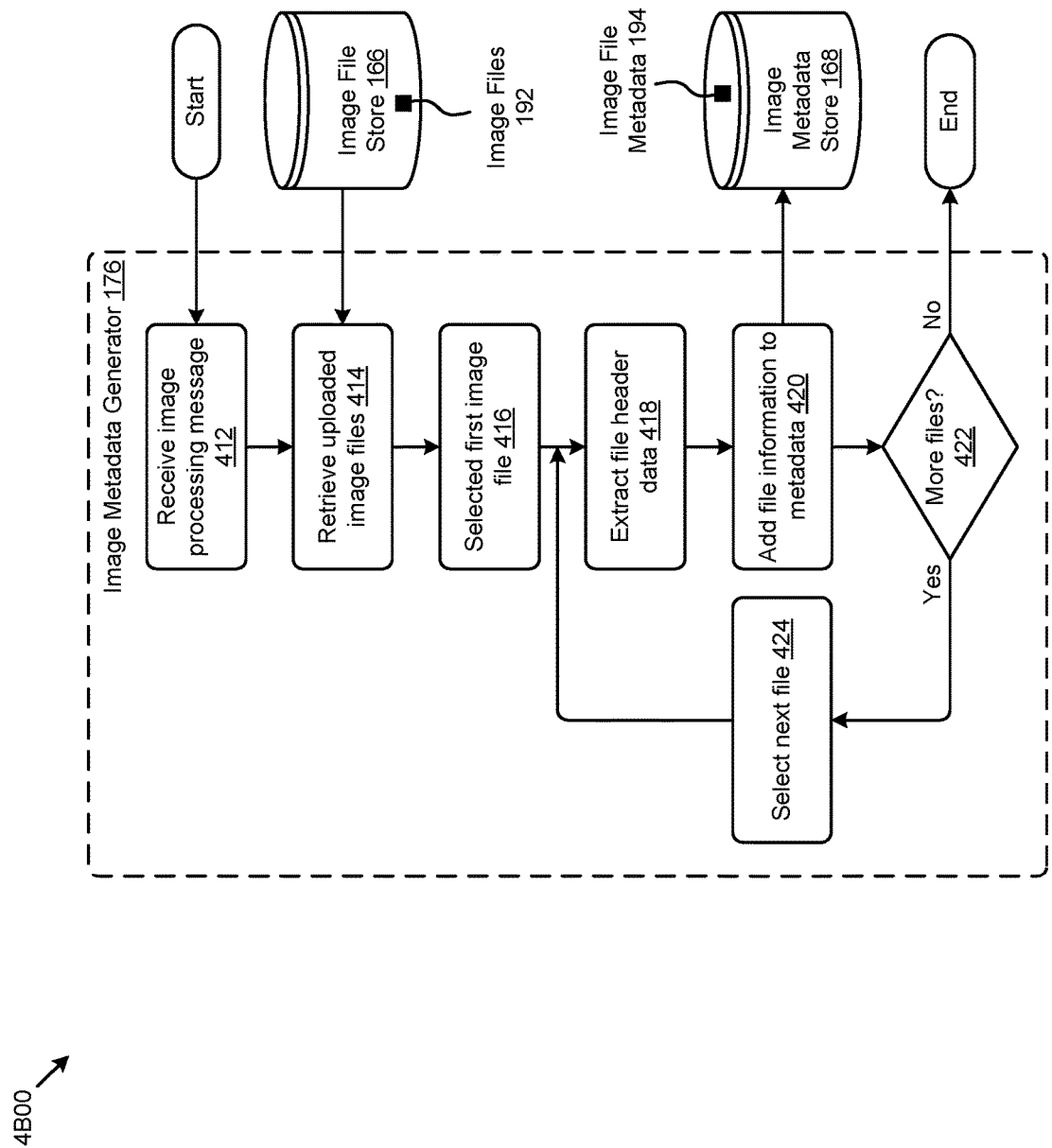
FIG. 4B presents a flow for generating metadata used by systems for using shared metadata to preserve logical associations between files when the files are physically stored in dynamically-determined cloud-based storage structures, according to some embodiments.

For each uploaded file, the metadata syntax 4A00 can have a respective row of values comprising the selected attributes of the file. The image file metadata 194 can then be used to quickly determine file associations for various purposes. As an example, the image file metadata 194 can describe certain associated files 402 that share a common PatientName="John Doe", StudyID="540", and SeriesID="542". For comparison, other approaches would iterate through all available files to determine the associated files 402, consuming significantly more computing resources and human resources (e.g., processing time). FIG. 4B presents a process flow for generating metadata such as described in the metadata syntax 4A00.

FIG. 4B presents a flow 4B00 for generating metadata used by systems for using shared metadata to preserve logical associations between files when the files are physically stored in dynamically-determined cloud-based storage structures. As an option, one or more instances of flow 4B00 or any aspect thereof may be implemented in the context of the architecture and functionality of the embodiments described herein. Also, the flow 4B00 or any aspect thereof may be implemented in any desired environment.

The flow 4B00 presents one embodiment of certain steps for generating metadata used by systems for using shared metadata to preserve logical associations between files when the files are physically stored in dynamically-determined cloud-based storage structures. In one or more embodiments, the steps and underlying operations comprising the flow 4B00 can be executed by the image metadata generator 176 in system 1B00. The image file store 166 and the image metadata store 168 from system 1B00 are also shown for reference. Specifically, flow 4B00 starts with the image metadata generator 176 receiving an image processing message (step 412) and retrieving uploaded image files (e.g., image files 192) in response to the image processing message (step 414). For example, the filename and location of the image files 192 and certain processing instructions can be included in the image processing message. The image metadata generator 176 can then select a first image file for processing (step 416) and proceed through certain processing steps execute for each retrieved file. Specifically, the image metadata generator 176 can extract the file header data from the selected file (step 418) and add the file information (e.g., attributes) to the image file metadata 194 in the image metadata store 168 (step 420). For example, each file can represent a row of information in the image file metadata 194 using the metadata syntax 4A00. The image metadata generator 176 can then check for additional files to process according to the image processing message (decision 422). When more files are available for processing, the image metadata generator 176 can select the next file (step 424) and repeat step 418 and step 420. When all files have been processed, the flow 4B00 can end. The generated metadata can then be used for quickly finding and rendering a large number of associated image files stored in various physical locations and directory structures as described in FIG. 5.

Figure 5:
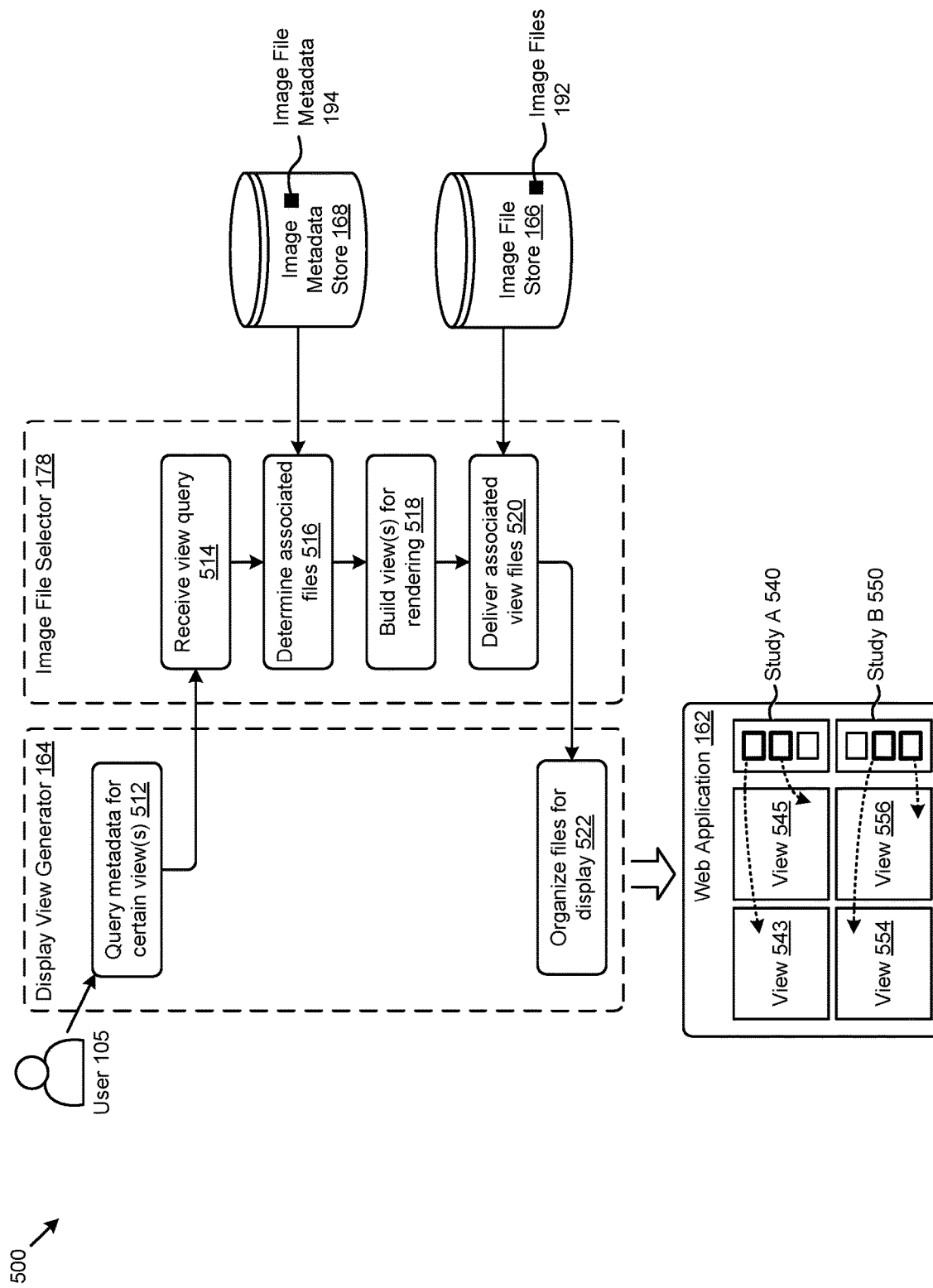
FIG. 5 presents a user image view selection process invoked in systems for using shared metadata to preserve logical associations between files when the files are physically stored in dynamically-determined cloud-based storage structures, according to an embodiment.

FIG. 5 presents a user image view selection process 500 invoked in systems for using shared metadata to preserve logical associations between files when the files are physically stored in dynamically-determined cloud-based storage structures. As an option, one or more instances of user image view selection process 500 or any aspect thereof may be implemented in the context of the architecture and functionality of the embodiments described herein. Also, the user image view selection process 500 or any aspect thereof may be implemented in any desired environment.

The user image view selection process 500 presents one embodiment of certain steps for using systems that use metadata to preserve logical associations between files when the files are physically stored in dynamically-determined cloud-based storage structures. In one or more embodiments, the steps and underlying operations comprising the user image view selection process 500 can be executed by the display view generator 164 and the image file selector 178 in system 1B00. The user 105, the image file store 166, and the image metadata store 168 from system 1B00 are also shown for reference. Specifically, user image view selection process 500 starts with the user 105 invoking the display view generator 164 to issue a metadata query for certain views desired by the user 105 (step 512). For example, the user 105 might want to compare Study A 540 and Study B 550 for a given patient. The image file selector 178 can receive the query (step 514) and determine the associated files pertaining the desired views (step 516). For example, the image file selector 178 can interpret the query on the image file metadata 194 in the image metadata store 168 to determine the associated files. Specifically, the query might request files associated with StudyID="A, B" and the image file selector 178 can determine the FileIDs having a value of "A" or a value of "B" in the StudyID column of the image file metadata 194. The image file selector 178 can then use the selected FileIDs to build the view objects to be used for rendering by the display view generator 164 (step 518). For example, step 518 might comprise the high-level logic shown in Table 1.

TABLE 1

| Ref | Logic Instruction(s) |
|-----|----------------------|
| 1 | foreach StudyID { |
| 2 | foreach FileID in StudyID { |
| 3 | getSeries(FileID); |
| 4 | add FileID to Series; |
| 5 | } |
| 6 | } |
| 7 | getSeries(file) { |
| 8 | if StudyID has Series { |
| 9 | return; } |
| 10 | else { |
| 11 | create new Series; |
| 12 | add Series to Study; |
| 13 | return; } |
| 14 | } |

The logic shown in Table 1 can build a programming code object representing the file identifiers and the file associations and relationships pertaining to the requested StudyID="Study A 540, Study B 550". Specifically, each study can have one or more corresponding views (e.g., series) comprising one or more image files. The image file selector 178 can then deliver the view objects and the associated files (step 520) to the display view generator 164 to be organized and displayed (step 522). For example, and as shown, the display view generator 164 can present in the web application 162 a view 543 and a view 545 corresponding to Study A 540, and a view 554 and a view 556 corresponding to the Study B 550.

Figure 6:
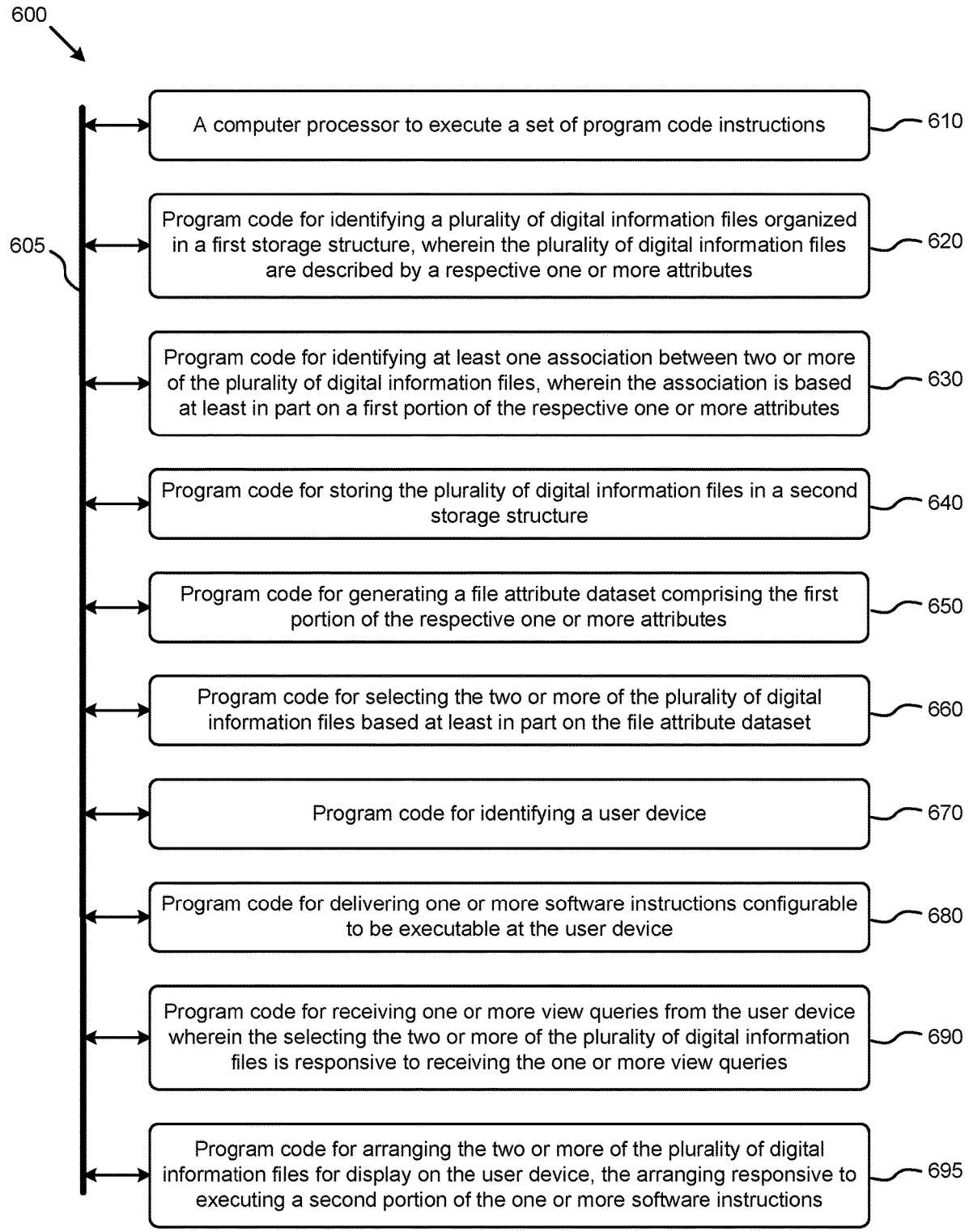
FIG. 6 depicts system components as arrangements of computing modules that are interconnected so as to implement certain of the herein-disclosed embodiments.

Additional Embodiments of the Disclosure
Additional Practical Application Examples FIG. 6 depicts a system 600 as an arrangement of computing modules that are interconnected so as to operate cooperatively to implement certain of the herein-disclosed embodiments. The partitioning of system 600 is merely illustrative and other partitions are possible. FIG. 6 depicts a block diagram of a system to perform certain functions of a computer system. As an option, the present system 600 may be implemented in the context of the architecture and functionality of the embodiments described herein. Of course, however, the system 600 or any operation therein may be carried out in any desired environment. The system 600 comprises at least one processor and at least one memory, the memory serving to store program instructions corresponding to the operations of the system. As shown, an operation can be implemented in whole or in part using program instructions accessible by a module. The modules are connected to a communication path 605, and any operation can communicate with other operations over communication path 605. The modules of the system can, individually or in combination, perform method operations within system 600. Any operations performed within system 600 may be performed in any order unless as may be specified in the claims. The shown embodiment implements a portion of a computer system, presented as system 600, comprising a computer processor to execute a set of program code instructions (module 610) and modules for accessing memory to hold program code instructions to perform: identifying a plurality of digital information files organized in a first storage structure, wherein the plurality of digital information files are described by metadata comprising respective one or more attributes (module 620); identifying at least one association between two or more of the plurality of digital information files, wherein the association is based at least in part on a first portion of the metadata (module 630); storing the plurality of digital information files in a second storage structure (module 640); generating a shared metadata file attribute dataset comprising the first portion of the respective one or more attributes (module 650); and selecting the two or more of the plurality of digital information files based at least in part on the file attribute dataset (module 660).

Some embodiments further include steps for identifying a user device (e.g., operated by a particular user), then delivering one or more software instructions configurable to be executable at the user device (module 670). The system receives one or more view queries from the user device. The system performs a selection of two or more of the plurality of digital information files (e.g., in response to receiving the one or more view queries). Views of the files are arranged on the user device, wherein the arrangement is responsive to executing a second portion of the one or more of the aforementioned software instructions. A different particular user at a different user device can view files that are arranged on the different user device, wherein the different particular user's arrangement is described by a portion of metadata comprising attributes and/or file associations between two or more of the plurality of digital information files.

In some embodiments, further steps include, delivering one or more software instructions configurable to be executable at the user device (module 680); receiving one or more view queries from the user device wherein the selecting the two or more of the plurality of digital information files is responsive to receiving the one or more view queries (module 690); and arranging the two or more of the plurality of digital information files for display on the user device, the arranging responsive to executing a second portion of the one or more software instructions (module 695).

System Architecture Overview
Additional System Architecture Examples

Figure 7A:
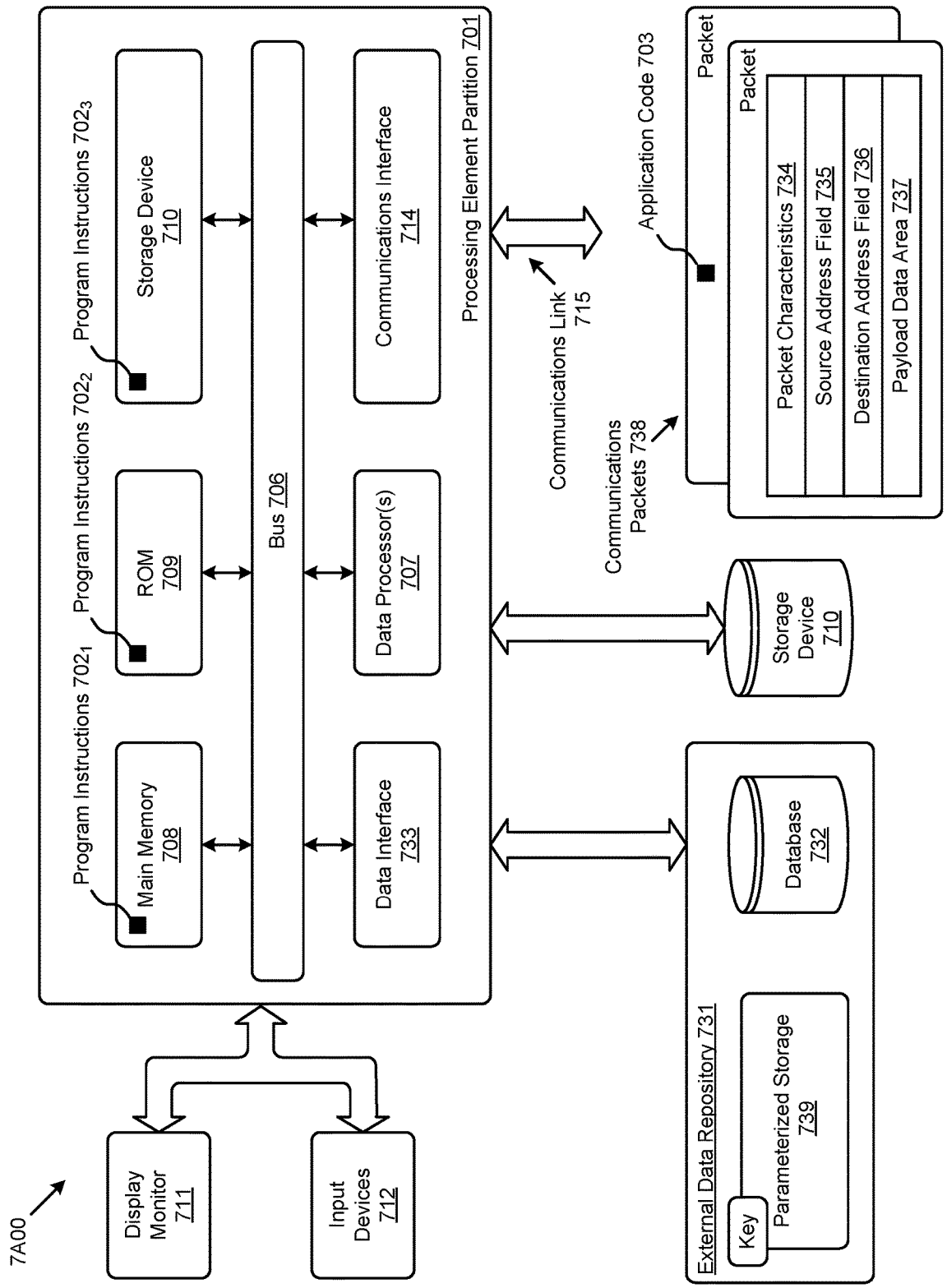
FIG. 7A and FIG. 7B depict exemplary architectures of components suitable for implementing embodiments of the present disclosure, and/or for use in the herein-described environments.

FIG. 7A depicts a block diagram of an instance of a computer system 7A00 suitable for implementing embodiments of the present disclosure. Computer system 7A00 includes a bus 706 or other communication mechanism for communicating information. The bus interconnects subsystems and devices such as a CPU, or a multi-core CPU (e.g., data processor 707), a system memory (e.g., main memory 708, or an area of random access memory RAM), a non-volatile storage device or non-volatile storage area (e.g., ROM 709), an internal or external storage device 710 (e.g., magnetic or optical), a data interface 733, a communications interface 714 (e.g., PHY, MAC, Ethernet interface, modem, etc.). The aforementioned components are shown within processing element partition 701, however other partitions are possible. The shown computer system 7A00 further comprises a display 711 (e.g., CRT or LCD), various input devices 712 (e.g., keyboard, cursor control), and an external data repository 731.

According to an embodiment of the disclosure, computer system 7A00 performs specific operations by data processor 707 executing one or more sequences of one or more program code instructions contained in a memory. Such instructions (e.g., program instructions $702_1$, program instructions $702_2$, program instructions $702_3$, etc.) can be contained in or can be read into a storage location or memory from any computer readable/usable medium such as a static storage device or a disk drive. The sequences can be organized to be accessed by one or more processing entities configured to execute a single process or configured to execute multiple concurrent processes to perform work. A processing entity can be hardware-based (e.g., involving one or more cores) or software-based, and/or can be formed using a combination of hardware and software that implements logic, and/or can carry out computations and/or processing steps using one or more processes and/or one or more tasks and/or one or more threads or any combination therefrom.

According to an embodiment of the disclosure, computer system 7A00 performs specific networking operations using one or more instances of communications interface 714. Instances of the communications interface 714 may comprise one or more networking ports that are configurable (e.g., pertaining to speed, protocol, physical layer characteristics, media access characteristics, etc.) and any particular instance of the communications interface 714 or port thereto can be configured differently from any other particular instance. Portions of a communication protocol can be carried out in whole or in part by any instance of the communications interface 714, and data (e.g., packets, data structures, bit fields, etc.) can be positioned in storage locations within communications interface 714, or within system memory, and such data can be accessed (e.g., using random access addressing, or using direct memory access DMA, etc.) by devices such as data processor 707.

The communications link 715 can be configured to transmit (e.g., send, receive, signal, etc.) any types of communications packets 738 comprising any organization of data items. The data items can comprise a payload data area 737, a destination address 736 (e.g., a destination IP address), a source address 735 (e.g., a source IP address), and can include various encodings or formatting of bit fields to populate the shown packet characteristics 734. In some cases the packet characteristics include a version identifier, a packet or payload length, a traffic class, a flow label, etc. In some cases the payload data area 737 comprises a data structure that is encoded and/or formatted to fit into byte or word boundaries of the packet.

In some embodiments, hard-wired circuitry may be used in place of or in combination with software instructions to implement aspects of the disclosure. Thus, embodiments of the disclosure are not limited to any specific combination of hardware circuitry and/or software. In embodiments, the term "logic" shall mean any combination of software or hardware that is used to implement all or part of the disclosure.

The term "computer readable medium" or "computer usable medium" as used herein refers to any medium that participates in providing instructions to data processor 707 for execution. Such a medium may take many forms including, but not limited to, non-volatile media and volatile media. Non-volatile media includes, for example, optical or magnetic disks such as disk drives or tape drives. Volatile media includes dynamic memory such as a random access memory.

Common forms of computer readable media includes, for example, floppy disk, flexible disk, hard disk, magnetic tape, or any other magnetic medium; CD-ROM or any other optical medium; punch cards, paper tape, or any other physical medium with patterns of holes; RAM, PROM, EPROM, FLASH-EPROM, or any other memory chip or cartridge, or any other non-transitory computer readable medium. Such data can be stored, for example, in any form of external data repository 731, which in turn can be formatted into any one or more storage areas, and which can comprise parameterized storage 739 accessible by a key (e.g., filename, table name, block address, offset address, etc.).

Execution of the sequences of instructions to practice certain embodiments of the disclosure are performed by a single instance of the computer system 7A00. According to certain embodiments of the disclosure, two or more instances of computer system 7A00 coupled by a communications link 715 (e.g., LAN, PTSN, or wireless network) may perform the sequence of instructions required to practice embodiments of the disclosure using two or more instances of components of computer system 7A00.

The computer system 7A00 may transmit and receive messages such as data and/or instructions organized into a data structure (e.g., communications packets 738). The data structure can include program instructions (e.g., application code 703), communicated through communications link 715 and communications interface 714. Received program code may be executed by data processor 707 as it is received and/or stored in the shown storage device or in or upon any other non-volatile storage for later execution. Computer system 7A00 may communicate through a data interface 733 to a database 732 on an external data repository 731. Data items in a database can be accessed using a primary key (e.g., a relational database primary key).

The processing element partition 701 is merely one sample partition. Other partitions can include multiple data processors, and/or multiple communications interfaces, and/or multiple storage devices, etc. within a partition. For example, a partition can bound a multi-core processor (e.g., possibly including embedded or co-located memory), or a partition can bound a computing cluster having plurality of computing elements, any of which computing elements are connected directly or indirectly to a communications link. A first partition can be configured to communicate to a second partition. A particular first partition and particular second partition can be congruent (e.g., in a processing element array) or can be different (e.g., comprising disjoint sets of components).

A module as used herein can be implemented using any mix of any portions of the system memory and any extent of hard-wired circuitry including hard-wired circuitry embodied as a data processor 707. Some embodiments include one or more special-purpose hardware components (e.g., power control, logic, sensors, transducers, etc.). A module may include one or more state machines and/or combinational logic used to implement or facilitate the performance characteristics of systems using shared metadata to preserve logical associations between files when the files are physically stored in dynamically-determined cloud-based storage structures.

Various implementations of the database 732 comprise storage media organized to hold a series of records or files such that individual records or files are accessed using a name or key (e.g., a primary key or a combination of keys and/or query clauses). Such files or records can be organized into one or more data structures (e.g., data structures used to implement or facilitate aspects of using shared metadata to preserve logical associations between files when the files are physically stored in dynamically-determined cloud-based storage structures). Such files or records can be brought into and/or stored in volatile or non-volatile memory.

Figure 7B:
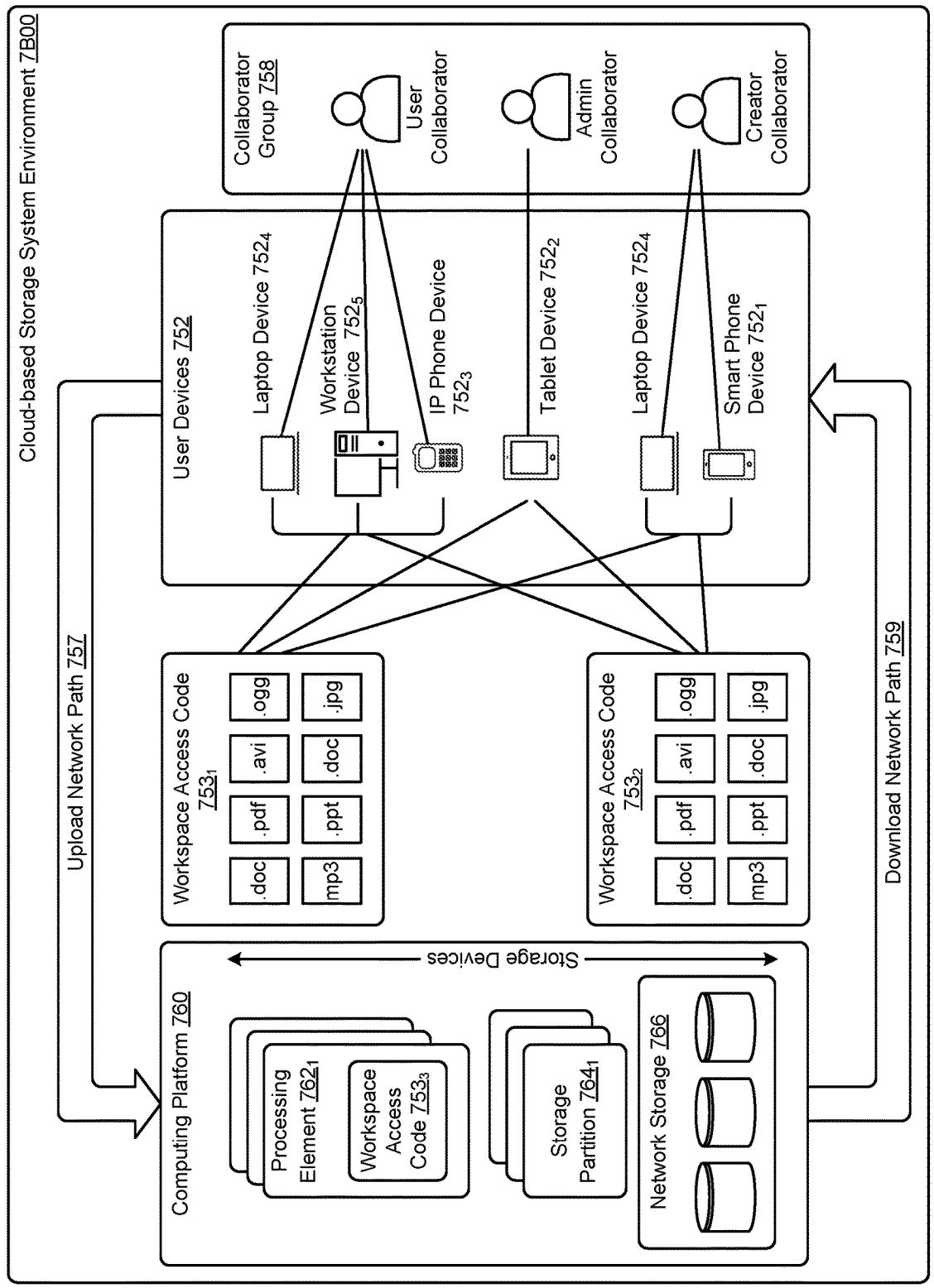

FIG. 7B depicts a block diagram of an instance of a cloud-based storage system environment 7B00. Such a cloud-based storage system environment supports access to workspaces through the execution of workspace access code (e.g., workspace access code $753_1$ and workspace access code $753_2$. Workspace access code can be executed on any of the shown user devices 752 (e.g., laptop device $752_4$, workstation device $752_5$, IP phone device $752_3$, tablet device $752_2$, smart phone device $752_1$, etc.). A group of users can form a collaborator group 758, and a collaborator group can be comprised of any types or roles of users. For example, and as shown, a collaborator group can comprise a user collaborator, an administrator collaborator, a creator collaborator, etc. Any user can use any one or more of the user devices, and such user devices can be operated concurrently to provide multiple concurrent sessions and/or other techniques to access workspaces through the workspace access code.

A portion of workspace access code can reside in and be executed on any user device. Also, a portion of the workspace access code can reside in and be executed on any computing platform (e.g., computing platform 760), including in a middleware setting. As shown, a portion of the workspace access code (e.g., workspace access code $753_3$) resides in and can be executed on one or more processing elements (e.g., processing element $762_1$). The workspace access code can interface with storage devices such the shown networked storage 766. Storage of workspaces and/or any constituent files or objects, and/or any other code or scripts or data can be stored in any one or more storage partitions (e.g., storage partition $764_1$). In some environments, a processing element includes forms of storage, such as RAM and/or ROM and/or FLASH, and/or other forms of volatile and non-volatile storage.

A stored workspace can be populated via an upload (e.g., an upload from a user device to a processing element over an upload network path 757). One or more constituents of a stored workspace can be delivered to a particular user and/or shared with other particular users via a download (e.g., a download from a processing element to a user device over a download network path 759).

In the foregoing specification, the disclosure has been described with reference to specific embodiments thereof. It will, however, be evident that various modifications and changes may be made thereto without departing from the broader spirit and scope of the disclosure. For example, the above-described process flows are described with reference to a particular ordering of process actions. However, the ordering of many of the described process actions may be changed without affecting the scope or operation of the disclosure. The specification and drawings to be regarded in an illustrative sense rather than in a restrictive sense.

What is claimed is:

1. A method comprising:
   maintaining a server in a cloud-based storage system;
   receiving an object at the server of the cloud-based storage system, the object being previously stored in a local storage directory structure of a device that is separate from the cloud-based storage system, and processing the object by:
     storing the object the cloud-based storage system in a cloud-based storage structure having a directory structure that is different from the local storage directory structure of the device that is separate from the cloud-based storage system, the object being stored as a digital information file,
     capturing directory information representing a location of the object within the local storage directory structure of the device that is separate from the cloud-based storage system, wherein the cloud-based storage system stores a plurality of digital information files for displaying one or more digital information views of respective objects, and
     the cloud-based storage system being accessible by both a first user and a second user, the one or more digital information views comprising different portions of the plurality of digital information files, the plurality of digital information files being organized in the cloud-based storage structure of the cloud-based storage system, wherein the plurality of digital information files are logically interrelated by respective one or more attributes for respective digital information files; and
   generating first image metadata from the respective one or more attributes for the first user to view the plurality of digital information files differently than the second user to view the plurality of digital information files using second image metadata, wherein generating image metadata comprises:
     identifying a first digital information view of the object for the first user, wherein the first digital information view corresponds to the local storage directory structure and is described by a respective first set of logical view attributes that are dynamically associated with the respective one or more attributes of a first portion of the plurality of digital information files organized in the cloud-based storage structure,
     generating the first image metadata comprising a first portion of metadata that describes the cloud-based storage structure and a second portion of metadata that describes the first digital information view of the object,
     identifying a second digital information view of the object for the second user, wherein the second digital information view corresponds to a second directory structure and is described by a respective second set of logical view attributes that are dynamically associated with the respective one or more attributes of a second portion of the plurality of digital information files organized in the cloud-based storage structure, wherein the second directory structure is different from both the local storage directory structure and the directory structure of the cloud-based storage structure,
     generating the second image metadata comprising the first portion of metadata that describes the cloud-based storage structure and a third portion of metadata that describes the second digital information view of the object, and
     delivering first digital information view of the object to the first user, where the first digital information view is delivered by providing the first image metadata to implement a first access model to overlay the local storage directory structure over the plurality of digital information files, and delivering second digital information view of the object to the second user, where the second digital information view is delivered by providing the second image metadata to implement a second access model to overlay the second directory structure over the plurality of digital information files.

2. The method of claim 1, further comprising:
   receiving one or more view queries comprising one or more view attributes from a user device, wherein the user device comprises one or more software instructions configurable to be executed at the user device; and
   selecting two or more of the plurality of digital information files based at least in part on the one or more view attributes of the one or more view queries and image metadata generated from the respective one or more attributes.

3. The method of claim 2, further comprising arranging the two or more of the plurality of digital information files for display on the user device, the arranging responsive to executing a second portion of the one or more software instructions.

4. The method of claim 2, wherein the one or more view queries are interpreted on the first image metadata or on the second image metadata.

5. The method of claim 1, wherein the plurality of digital information files are medical image files.

6. The method of claim 1, wherein the plurality of digital information files comprise header data describing the respective one or more attributes.

7. The method of claim 1, wherein the cloud-based storage structure comprises a plurality of directory structures that correspond to a plurality of data nodes.

8. A computer readable medium, embodied in a non-transitory computer readable medium, the non-transitory computer readable medium having stored thereon a sequence of instructions which, when stored in memory and executed by a processor causes the processor to perform a set of acts, the set of acts comprising:
   maintaining a server in a cloud-based storage system;
   receiving an object at the server of in the cloud-based storage system, the object being previously stored in a local storage directory structure of a device that is separate from the cloud-based storage system, and processing the object by:
     storing the object into the cloud-based storage system in a cloud-based storage structure having a directory structure that is different from the local storage directory structure of the device that is separate from the cloud-based storage system, the object being stored as a digital information file, capturing directory information representing a location of the object within the local storage directory structure of the device that is separate from the cloud-based storage system, wherein the cloud-based storage system stores a plurality of digital information files for displaying one or more digital information views of respective objects, and the cloud-based storage system being accessible by both a first user and a second user, the one or more digital information views comprising different portions of the plurality of digital information files, the plurality of digital information files being organized in the cloud-based storage structure of the cloud-based storage system, wherein the plurality of digital information files are logically interrelated by respective one or more attributes for respective digital information files; and generating first image metadata from the respective one or more attributes for the first user to view the plurality of digital information files differently than the second user to view the plurality of digital information files using second image metadata, wherein generating image metadata comprises:

identifying a first digital information view of the object for the first user, wherein the first digital information view corresponds to the local storage directory structure and is described by a respective first set of logical view attributes that are dynamically associated with the respective one or more attributes of a first portion of the plurality of digital information files organized in the cloud-based storage structure, generating the first image metadata comprising a first portion of metadata that describes the cloud-based storage structure and a second portion of metadata that describes the first digital information view of the object, identifying a second digital information view of the object for the second user, wherein the second digital information view corresponds to a second directory structure and is described by a respective second set of logical view attributes that are dynamically associated with the respective one or more attributes of a second portion of the plurality of digital information files organized in the cloud-based storage structure, wherein the second directory structure is different from both the local storage directory structure and the directory structure of the cloud-based storage structure, generating the second image metadata comprising the first portion of metadata that describes the cloud-based storage structure and a third portion of metadata that describes the second digital information view of the object, and delivering first digital information view of the object to the first user, where the first digital information view is delivered by providing the first image metadata to implement a first access model to overlay the local storage directory structure over the plurality of digital information files, and delivering second digital information view of the object to the second user, where the second digital information view is delivered by providing the second image metadata to implement a second access model to overlay the second directory structure over the plurality of digital information files.

9. The computer readable medium of claim 8, further comprising instructions which, when stored in the memory and executed by the processor causes the processor to perform acts of:

receiving one or more view queries comprising one or more view attributes from a user device, wherein the user device comprises one or more software instructions configurable to be executed at the user device; and selecting two or more of the plurality of digital information files based at least in part on the one or more view attributes of the one or more view queries and image metadata generated from the respective one or more attributes.

10. The computer readable medium of claim 9, further comprising instructions which, when stored in memory and executed by the processor causes the processor to perform acts of arranging the two or more of the plurality of digital information files for display on the user device, the arranging responsive to executing a second portion of the one or more software instructions.

11. The computer readable medium of claim 9, wherein the one or more view queries are interpreted on the first image metadata or on the second image metadata.

12. The computer readable medium of claim 8, wherein the plurality of digital information files are medical image files.

13. The computer readable medium of claim 8, wherein the plurality of digital information files comprise header data describing the respective one or more attributes.

14. The computer readable medium of claim 8, wherein the cloud-based storage structure comprises a plurality of directory structures that correspond to a plurality of data nodes.

15. A system comprising:
a storage medium having stored thereon a sequence of instructions; and
a processor or processors that execute the sequence of instructions to cause the processor or processors to perform a set of acts, the set of acts comprising,
maintaining a server in a cloud-based storage system;
receiving an object at the server of the cloud-based storage system, the object being previously stored in a local storage directory structure of a device that is separate from the cloud-based storage system, and processing the object by:
storing the object into the cloud-based storage system in a cloud-based storage structure having a directory structure that is different from the local storage directory structure of the device that is separate from the cloud-based storage system, the object being stored as a digital information file,
capturing directory information representing a location of the object within the local storage directory structure of the device that is separate from the cloud-based storage system, wherein the cloud-based storage system stores a plurality of digital information files for displaying one or more digital information views of respective objects, and
the cloud-based storage system being accessible by both a first user and a second user, the one or more digital information views comprising different portions of the plurality of digital information files, the plurality of digital information files being organized in the cloud-based storage structure of the cloud-based storage system, wherein the plurality of digital information files are logically interrelated by respective one or more attributes for respective digital information files; and generating first image metadata from the respective one or more attributes for the first user to view the plurality of digital information files differently than the second user to view the plurality of digital information files using second image metadata, wherein generating image metadata comprises:

identifying a first digital information view of the object for the first user, wherein the first digital information view corresponds to the local storage directory structure and is described by a respective first set of logical view attributes that are dynamically associated with the respective one or more attributes of a first portion of the plurality of digital information files organized in the cloud-based storage structure, generating the first image metadata comprising a first portion of metadata that describes the cloud-based storage structure and a second portion of metadata that describes the first digital information view of the object, identifying a second digital information view of the object for the second user, wherein the second digital information view corresponds to a second directory structure and is described by a respective second set of logical view attributes that are dynamically associated with the respective one or more attributes of a second portion of the plurality of digital information files organized in the cloud-based storage structure, wherein the second directory structure is different from both the local storage directory structure and the directory structure of the cloud-based storage structure, generating the second image metadata comprising the first portion of metadata that describes the cloud-based storage structure and a third portion of metadata that describes the second digital information view of the object, and delivering first digital information view of the object to the first user, where the first digital information view is delivered by providing the first image metadata to implement a first access model to overlay the local storage directory structure over the plurality of digital information files, and delivering second digital information view of the object to the second user, where the second digital information view is delivered by providing the second image metadata to implement a second access model to overlay the second directory structure over the plurality of digital information files.

16. The system of claim 15, wherein the plurality of digital information files are medical image files composed of hierarchical image tiles.

17. The system of claim 15, wherein the cloud-based storage structure comprises a plurality of directory structures that correspond to a plurality of data nodes.

18. The system of claim 15, further comprising instructions to cause the processor or processors to perform the set of acts, the set of acts further comprising:

receiving one or more view queries comprising one or more view attributes from a user device, wherein the user device comprises one or more software instructions configurable to be executed at the user device; and selecting two or more of the plurality of digital information files based at least in part on the one or more view attributes of the one or more view queries and image metadata generated from the respective one or more attributes.

19. The system of claim 18, further comprising instructions to cause the processor or processors to perform the set of acts, the set of acts further comprising arranging the two or more of the plurality of digital information files for display on the user device, the arranging responsive to executing a second portion of the one or more software instructions.

20. The system of claim 18, wherein the one or more view queries are interpreted on the first image metadata or on the second image metadata.

21. The system of claim 15, wherein the plurality of digital information files comprise header data describing the respective one or more attributes.

* * * * *